United States Patent
Hegg et al.

(10) Patent No.: US 11,267,838 B2
(45) Date of Patent: Mar. 8, 2022

(54) METHODS FOR LIGNIN DEPOLYMERIZATION USING THIOLS

(71) Applicant: BOARD OF TRUSTEES OF MICHIGAN STATE UNIVERSITY, East Lansing, MI (US)

(72) Inventors: Eric Linke Hegg, East Lansing, MI (US); James E. Jackson, Haslett, MI (US); Grace Elizabeth Klinger, Lansing, MI (US)

(73) Assignee: BOARD OF TRUSTEES OF MICHIGAN STATE UNIVERSITY, East Lansing, MI (US)

( * ) Notice: Subject to any disclaimer, the term of this patent is extended or adjusted under 35 U.S.C. 154(b) by 18 days.

(21) Appl. No.: 16/603,328

(22) PCT Filed: Apr. 17, 2018

(86) PCT No.: PCT/US2018/027846
§ 371 (c)(1),
(2) Date: Oct. 7, 2019

(87) PCT Pub. No.: WO2018/195000
PCT Pub. Date: Oct. 25, 2018

(65) Prior Publication Data
US 2020/0048292 A1 Feb. 13, 2020

Related U.S. Application Data

(60) Provisional application No. 62/486,143, filed on Apr. 17, 2017.

(51) Int. Cl.
*C07G 1/00* (2011.01)
*C07C 37/54* (2006.01)
(Continued)

(52) U.S. Cl.
CPC .............. *C07G 1/00* (2013.01); *C07C 37/54* (2013.01); *C07C 41/01* (2013.01); *C07C 45/65* (2013.01); *C25B 3/25* (2021.01)

(58) Field of Classification Search
CPC .................... C07G 1/00; C07C 37/54
See application file for complete search history.

(56) References Cited

U.S. PATENT DOCUMENTS 3,951,732 A * 4/1976 Sjostrom .............. D21C 9/1036
162/65
4,072,584 A 2/1978 Cipris et al.
(Continued)

FOREIGN PATENT DOCUMENTS

WO WO-2011/003029 A2 1/2011
WO WO-2012/036884 A2 3/2012

OTHER PUBLICATIONS

Rothwarf et al. (Proc. Natl. Acad. Sci. USA, vol. 89, 7944-7948, 1992) (Year: 1992).*
(Continued)

*Primary Examiner* — Liam J Heincer
(74) *Attorney, Agent, or Firm* — Marshall, Gerstein & Borun LLP

(57) ABSTRACT

The disclosure relates to a method for depolymerizing lignin. The method includes reacting a lignin compound with a thiol compound to depolymerize the lignin compound and to form a depolymerized lignin product having a reduced molecular weight relative to the lignin compound prior to reacting. The method can further include forming an oxidized thiol reaction product between two thiol groups from one or more thiol compounds, and then reducing the oxidized thiol reaction product to re-form or regenerate the thiol compound for further lignin depolymerization.

18 Claims, 11 Drawing Sheets

(51) Int. Cl.
*C07C 41/01* (2006.01)
*C07C 45/65* (2006.01)
*C25B 3/25* (2021.01)

(56) References Cited

U.S. PATENT DOCUMENTS

| | | | | |
|---|---|---|---|---|
| 5,128,253 | A * | 7/1992 | Labuda | C12P 7/24 |
| | | | | 435/147 |
| 8,304,213 | B2 | 11/2012 | Diner et al. | |
| 9,150,842 | B2 | 10/2015 | Johansen et al. | |
| 9,359,391 | B2 | 6/2016 | Stahl et al. | |
| 2009/0004697 | A1* | 1/2009 | Koltermann | C12P 19/24 |
| | | | | 435/72 |
| 2009/0130707 | A1 | 5/2009 | Xu | |
| 2010/0159517 | A1* | 6/2010 | Diner | C08H 8/00 |
| | | | | 435/72 |
| 2012/0107886 | A1 | 5/2012 | Albizati et al. | |
| 2012/0192860 | A1 | 8/2012 | Dhepe et al. | |
| 2012/0196353 | A1 | 8/2012 | Chatterjee et al. | |
| 2013/0189747 | A1 | 7/2013 | Xu | |
| 2014/0069822 | A1 | 3/2014 | Kraj et al. | |
| 2014/0147895 | A1 | 5/2014 | Gaspar et al. | |
| 2014/0275501 | A1 | 9/2014 | Capanema et al. | |
| 2014/0288285 | A1* | 9/2014 | Ters | C08H 6/00 |
| | | | | 530/500 |
| 2015/0099868 | A1 | 4/2015 | Yang et al. | |
| 2015/0322214 | A1 | 11/2015 | Singh et al. | |
| 2015/0361616 | A1 | 12/2015 | Essaddam | |
| 2016/0187345 | A1* | 6/2016 | Ralph | C07C 69/734 |
| | | | | 436/63 |
| 2016/0244894 | A1 | 8/2016 | Ottonello et al. | |
| 2017/0152199 | A1* | 6/2017 | Feghali | C07C 37/055 |

OTHER PUBLICATIONS

Gall et al., Stereochemical features of glutathione-dependent enzymes in the *Sphingobium* sp. strain SYK-6 β-aryl etherase pathway, J. Biol. Chem., 289(12):8656-67 (Mar. 2014).
International Application No. PCT/US18/27846, International Search Report and Written Opinion, dated Jul. 9, 2018.
Klinger et al., Biomimetic Reductive Cleavage of Keto Aryl Ether Bonds by Small-Molecule Thiols, ChemSusChem. (Aug. 16, 2019).
Masai et al., A bacterial enzyme degrading the model lignin compound beta-etherase is a member of the glutathione-S-transferase superfamily, FEBS Lett., 323(1-2):135-40 (May 1993).
Tolbert et al., Characterization and analysis of the molecular weight of lignin for biorefining studies, Biofuels, Bioproducts & Biorefining, 8:1-21 (Jun. 2014).
Wariishi et al., Thiol-mediated oxidation of nonphenolic lignin model compounds by manganese peroxidase of Phanerochaete chrysosporium, J. Biol. Chem., 264(24):14185-91 (Aug. 1989).
Klinger et al., Mild organic catalyst for the depolymerization of lignin, presented at Symposium on Biotechnology for Fuels and Chemicals, San Francisco, CA (May 1, 2017).

"Scientists mimic natural decay to break down plant material for biofuel production", Great Lakes Bioenergy Research Center, Press Release, Sep. 9, 2019.
Botte, Electrochemical Manufacturing in the Chemical Industry. The Electrochemical Society-Interface. 2014, 49-55.
Crestini et al., Immobilized methyltrioxo rhenium (MTO)/H2O2 systems for the oxidation of lignin and lignin model compounds, Bioorg Med Chem. 2006, 14, 5292-5302.
Dale et al., The Need for Biofuels. Chem Eng Prog. 2015, 111, 36-40.
Glass et al., Chapter 27: Sulfur-, Selenium-, and Tellurium-Containing Compounds. Organic Electrochemistry, 5th ed; Hammerich, O.; Speiser, B.; CRC Press—Taylor & Francis Group: Boca Raton, Florida, 2015; pp. 1035-1102.
Harmsen et al., Literature Review of Physical and Chemical Pretreatment Processes for Lignocellulosic Biomass. Biosynergy Project Review. 2010, 1-49.
Helmich et al., Structural Basis of Stereospecificity in the Bacterial Enzymatic Cleavage of 13-Aryl Ether Bonds in Lignin. J. Biol Chem. 2016, 291, 5234-5246.
Hu et al., Chemical Groups and Structural Characterization of Lignin via Thiol-Mediated Demethylation. J Wood Chem Technol. 2014, 34, 122-134.
Lange et al., Oxidative upgrade of lignin-Recent routes reviewed. Eur Polym J. 2013, 49, 1151-1173.
Layton, A Comparison of Energy Densities of Prevalent Energy Sources in Units of Joules Per Cubic Meter. Inter J Green Energy. 2008, 5, 438-455.
Li et al., Catalytic Transformation of Lignin for the Production of Chemicals and Fuels. Chem Rev. 2015, 115, 11559-11624.
Mota et al., Recovery of Vanillin and Syringaldehyde from Lignin Oxidation: A Review of Separation and Purification Processes. Sep Purif Rev. 2016, 45, 227-259.
Nagieb, Demethylation of thiolignin by reaction with potassium dichromate—a kinetic study. Wood Sci Technol. 1985, 19, 233-242.
Picart et al., From gene to biorefinery: microbial beta-etherases as promising biocatalysts for lignin valorization, Front Microbiol. 2015, 6, 1-8.
Rolando et al., Chapter 6/Section 6.4: Thioacidolysis. Wood Science: Methods in Lignin Chemistry. Lin, S.Y.; Pence, C.W.; Springer: Verlag Berlin Heidelberg, 1992; pp. 334-349.
Sequeira et al., Electrochemical Routes for Industrial Synthesis. J Braz Chem Soc. 2009, 20, 387-406.
Trott et al., AutoPock Vina: improving the speed and accuracy of docking with a new scoring function, efficient optimization and multithreading. J Comput Chem. 2010, 31, 455-461.
Vepejs et al., Thioaldehyde Piels-Alder Reactions, J. Org. Chem. 1986, 51, 1556-1562.
Wong, Structre and Action Mechanism of Ligninolytic Enzymes. Appl Biochem Biotechnol. 2009, 157, 174-209.
Zucca et al., Biomimetic metalloporphines and metalloporphyrins as potential tools for delignification: Molecular mechanisms and application perspectives. J Mol Catal A—Chem. 2014, 388-389, 2-34.

* cited by examiner $R_1 = H, OH; R_2 \& R_3 = H, OCH_3; R_4 = H, CH_2OH; R_5 \& R_6 = H, OCH_3$

| Dimer | Thiol | Solvent | Mole Ratio | Temp (°C) | Time (hrs) | % Conv. | 1 | 2 |
|---|---|---|---|---|---|---|---|---|
| (phenacyl phenyl ether structure) | BME | Neat | | 100 | 3 | 85 | 73 | 75 |
| | BME | MeCN | 1:1 | Reflux | 24 | 14 | 8 | 6 |
| | BME | MeCN | 1:2 | Reflux | 24 | 34 | 23 | 27 |
| | BME | MeCN | 1:10 | Reflux | 22 | 48 | 34 | 40 |
| | BME | MeCN | 1:100 | Reflux | 24 | 94 | 75 | 85 |
| | BME | MeCN | 1:10 | 50 | 24 | 7 | 2 | 1 |
| | BME | MeCN | 1:10 | RT | 24 | 1 | 0 | 3 |
| | BME | MeOH | 1:10 | Reflux | 24 | 30 | 1 | 16 |
| | BME | MeOH | 1:10 | 40 | 12 | 11 | 1 | 4 |
| | BME | MeOH | 1:10 | RT | 24 | 1 | 0 | 2 |
| | BME | DMF | 1:10 | Reflux | 4 | 96 | 90 | >100* |
| | BME | DMF | 1:10 | 100 | 24 | 97 | 70 | 56 |
| | BME | DMF | 1:10 | 50 | 24 | 94 | 53 | 61 |
| | BME | DMF | 1:10 | RT | 48 | 77 | 44 | 49 |
| | BME | NMP | 1:10 | Reflux | 2 | 88 | 73 | >100* |
| | BME | NMP | 1:10 | 100 | 12 | 94 | 66 | 87 |
| | BME | NMP | 1:10 | 50 | 12 | 40 | 19 | 22 |
| | BME | NMP | 1:10 | RT | 24 | 6 | 1 | 1 |
| | BME | DMSO | 1:10 | 100 | 4 | 99 | 81 | 99 |
| | BME | DMSO | 1:10 | 50 | 12 | 80 | 36 | 25 |
| | BME | DMSO | 1:10 | RT | 24 | 38 | 16 | 7 |
| | DTT | Neat | | 100 | 3 | 85 | 48 | 62 |
| | DTT | MeCN | 1:1 | Reflux | 24 | 18 | 6 | 13 |
| | DTT | MeCN | 1:2 | Reflux | 24 | 69 | 47 | 53 |
| | DTT | MeCN | 1:10 | Reflux | 24 | 55 | 25 | 34 |
| | DTT | MeCN | 1:100 | Reflux | 24 | 34 | 29 | 31 |
| | DTT | MeOH | 1:2 | Reflux | 24 | 3 | 2 | 0 |
| | DTT | DMF | 1:2 | 100 | 24 | 57 | 15 | 56 |
| | DTT | NMP | 1:2 | 100 | 24 | 94 | 5 | 71 |
| | DTT | DMSO | 1:2 | 100 | 2 | 98 | 73 | 78 |
| | Thiophenol | Neat | | 100 | 6 | - | - | 5 |
| | Thiophenol | MeCN | 1:1 | Reflux | 24 | 30 | 4 | 16 |
| | Thiophenol | MeCN | 1:2 | Reflux | 24 | 95 | 5 | 69 |
| | Thiophenol | MeCN | 1:10 | Reflux | 24 | 100 | 26 | 46 |
| | Thiophenol | MeCN | 1:100 | Reflux | - | - | - | - |

FIG. 3A

| | | | | | | | |
|---|---|---|---|---|---|---|---|
| Percent Yield of Lignin Dimer Cleavage | | | | | | | |
| Glutathione | | MeCN | 1:1 | Reflux | 48 | 45 | 3 | 38 |
| | | MeCN | 1:2 | Reflux | 48 | 39 | 0 | 33 |
| | | MeCN | 1:10 | Reflux | 48 | 25 | 0 | 10 |
| | | MeCN | 1:100 | Reflux | 48 | 9 | 1 | 3 |
| 1,3-Propanedithiol | | Neat | | 100 | 3 | 23 | 15 | 15 |
| | | MeCN | 1:1 | Reflux | 24 | 8 | 2 | 7 |
| | | MeCN | 1:2 | Reflux | 24 | 12 | 4 | 10 |
| | | MeCN | 1:10 | Reflux | 2 | 24 | 17 | 19 |
| | | MeCN | 1:100 | Reflux | 8 | 98 | 90 | 94 |
| | | MeOH | 1:100 | Reflux | 24 | 15 | 12 | 0 |
| | | DMF | 1:100 | 100 | 2 | 100 | 84 | 86 |
| | | NMP | 1:100 | 100 | 4 | 100 | 80 | 91 |
| | | DMSO | 1:100 | 100 | 2 | 100 | 93 | 98 |
| | BME | Neat | | 100 | 48 | 31 | 0 | 0 |
| | | MeCN | 1:10 | Reflux | 48 | 2 | 0 | 0 |
| | DTT | Neat | | 100 | 48 | 2 | 0 | 1 |
| | | MeCN | 1:2 | Reflux | 48 | 1 | 0 | 0 |
| | BME | Neat | | 100 | 48 | 99 | 13 | 25 |
| | | MeCN | 1:10 | Reflux | 48 | 43 | 4 | 18 |
| | DTT | Neat | | 100 | 48 | 100 | 0 | 15 |
| | | MeCN | 1:2 | Reflux | 48 | 11 | 3 | <1 |
| | BME | Neat | | 100 | 48 | 96 | 1 | 33 |
| | | MeCN | 1:10 | Reflux | 48 | 97 | 29 | 23 |
| | DTT | Neat | | 100 | 48 | 100 | 0 | 31 |
| | | MeCN | 1:2 | Reflux | 12 | 20 | 14 | 9 |
| | BME | Neat | | 100 | 48 | 90 | 23 | 82 |
| | | MeCN | 1:10 | Reflux | 24 | 100 | 3 | 23 |
| | DTT | Neat | | 100 | 48 | 100 | 64 | 35 |
| | | MeCN | 1:2 | Reflux | 48 | 100 | 1 | 27 |

METHODS FOR LIGNIN DEPOLYMERIZATION USING THIOLS

CROSS REFERENCE TO RELATED APPLICATION

This application is a National Stage application of International Application No. PCT/US2018/027846, filed Apr. 17, 2018, which claims priority to U.S. Provisional Patent Application No. 62/486,143, filed Apr. 17, 2017, the entire disclosures of which are incorporated herein by reference.

STATEMENT OF GOVERNMENT INTEREST

This invention was made with government support under DE-FC02-07ER64494 awarded by the U.S. Department of Energy. The government has certain rights in the invention.

FIELD OF THE DISCLOSURE

The disclosure relates to methods for depolymerizing lignin using thiols to form a reduced molecular weight lignin product. Lignin depolymerization products such as aromatics, alcohols, aldehydes, and ketones can be used as feedstocks for bio-renewable fuels and bio-renewable chemicals. Current techniques for lignin degradation include pyrolysis, acid- or base-catalyzed depolymerization, oxidation, gasification, and enzyme-catalyzed degradation.

BACKGROUND

The energy problem the world is faced with today stems from the amount of kilowatts consumed per person coupled with the rising population and the decline of fossil fuel resources supplying the kilowatt energy. Globally, 39% of the energy consumed is in the form of electric power while 27% is used for transportation, separating the energy problem into two classes: service energy and mobile energy, both of which have in the past been supplied by fossil sources. The service energy, primarily heat, refrigeration, and light, is provided by electricity. The traditionally fossil sources of this energy can be and are being replaced by renewable energies in the form of wind, solar, photovoltaics, etc. The second group, the mobile energy, represents the liquid fuels used to power trains, planes, automobiles, ships, etc. This mobile energy from energy-rich liquid fuels cannot be as easily replaced by non-liquid forms of renewable sources as the service energy group.

To tackle this liquid energy problem, research has turned to plants. Just as fossilized plants have given rise to the petroleum industry, current vegetative growth in the form of lignocellulosic biomass has given rise to the liquid-biofuel industry. It is here where research has reached a bottleneck in affordable and efficient means to turn plants into liquid fuels. In order to reach energy consumption demands, the whole plants must be utilized. Currently, in lignocellulosic biomass processing, cellulose and hemicellulose are the typical desired products due to their ability to be fermented into ethanol for production of fuel, paper, rayon, cellulose acetate, etc. However, over 50% of the plant remains unprocessed including sugar monomers that currently cannot be easily converted to ethanol, and lignin, an aromatic polymer that gives plants their structure. Current research aims to engineer microbes for digestion of non-digestible sugars, but that still leaves lignin, which contains roughly 50% of the plant's energy.

Lignin is a complex organic polymer structure that is comprised of various aromatic subunits. These building blocks are covalently connected, most frequently by ether linkages which can comprise two-thirds or greater of the total linkages. The complexity of lignin is due to its non-linear crosslinking via roughly six different chemical linking motifs. One illustration of the crosslinked nature of lignin is shown in FIG. 1, panel (A), which includes a representative distribution of the linkages present in the lignin of a typical hardwood.

The dominant form of the linkages in lignin is the β-O-4 ether linkage, which accounts for approximately 43-50% of lignin linkages in softwood to up to 70% in hybrid poplar. The remaining linkages are divided among a variety of carbon-carbon and ether (carbon-oxygen) bonds, depending on the lignin source.

To process and break down lignin for uses in energy or value-added products, current techniques include pyrolysis, base or acid catalyzed depolymerization, oxidation, and gasification, for example. Despite the significant advances that have been made, a simple and inexpensive process that produces few side reactions is still needed to make lignin depolymerization cost effective. One area of research in particular is the use of enzymes to catalyze the degradation of lignin.

Biological sources such as bacteria and white-rot fungi have been found to degrade lignin via enzymatic pathways. For example, white-rot fungi produce four types of metalloenzymes that cleave lignin via oxidation: laccase, lignin peroxidase, manganese peroxidase, and versatile peroxidase. Laccase has low substrate specificity and contains four copper sites that are involved in four one-electron oxidations of a reducing substrate, effecting two two-electron reductions of dioxygen to water and formation of radical substrates. Lignin peroxidase works via a heme and mediator mechanism, which involves two steps. The first is the addition of hydrogen peroxide and a two-electron oxidation of the heme. The second is two one-electron reductions of the heme from a mediator, veratryl alcohol, resulting in radical cation formation veratryl alcohol, which in turn oxidizes the lignin substrates. The manganese peroxidase mechanism is similar but instead of a mediator shunting electrons from the active site to the lignin polymer via veratryl alcohol, this enzyme uses manganese. Addition of hydrogen peroxide oxidizes the heme of the enzyme which is reduced by manganese. The oxidized manganese can then in turn oxidize aromatic components of lignin. The last metalloenzyme is versatile peroxidase which is a natural enzyme hybrid between manganese peroxidase and lignin peroxidase. In all these cases, the lignin is oxidized and cleaved into smaller fragments. Once fragmented, other enzymes can, via various mechanisms, degrade the fragments into what is eventually tricarboxylic acid cycle intermediates. These enzymes come from a range of organisms and from a variety of enzyme classes including carboxylases, lyases, dehydrogenases, and many others.

Much of enzymatic lignin degradation research has focused on cleavage of the β-O-4 ether linkage, the most prevalent linkage in lignin. Examples of β-etherases that can effectively cleave this ether linkage have been reported in the fungi genus *Chaetomium*, as well as in the gram negative soil bacteria *Sorangium cellulosum*, and two marine microorganism species in the *Novosphingobium* genus. The most studied, however, is a species in the *Sphingobium* genius, sp. SYK-6. *Sphingobium*, sp. SYK-6 was first isolated from the waste streams of paper manufacturing, and until recently has been the sole example of an organism capable of the β-O-4 cleavage pathway.

From these sources, β-etherases were found to have the enzymatic activity to cleave the β-aryl ether bond in lignin. Protein structure studies revealed that β-etherases catalyze lignin depolymerization using a sulfur-containing moiety in the enzyme active site. However, in a laboratory setting, success with β-etherases has been slow, encountering issues such as different lignin morphologies (e.g., -methoxy groups ortho to the —OH of the phenol ring) affecting enzyme activity.

More efficient, affordable, green methods of lignin deconstruction into its building blocks are needed to yield commercially viable chemical compounds such as aromatics, alcohols, aldehydes, etc., and thereby to fully utilize plant energy as a means of replacing fossil fuels for use in chemicals and liquid fuels.

SUMMARY

In one embodiment, the disclosure relates to a method for depolymerizing lignin, the method comprising: reacting a lignin compound with a thiol compound to depolymerize the lignin compound and to form a depolymerized lignin product having a reduced molecular weight relative to the lignin compound prior to reacting.

In another embodiment, the disclosure relates to a method for depolymerizing lignin, the method comprising: reacting a lignin compound with a thiol compound to depolymerize the lignin compound and to form (i) a depolymerized lignin product having a reduced molecular weight relative to the lignin compound prior to reacting, and (ii) an oxidized thiol reaction product between two thiol groups from one or more thiol compounds; and reducing the oxidized thiol reaction product to re-form the thiol compound; wherein: the lignin compound comprises a cross-linked phenolic polymer comprising β-O-4 ether linkages, and the depolymerized lignin product has fewer β-O-4 ether linkages between phenolic monomer units in the cross-linked phenolic polymer relative to the lignin compound prior to reacting; the depolymerized lignin product has a molecular weight of 50% or less, or 60% or less, relative to the molecular weight of the lignin compound prior to reacting; and the depolymerized lignin product comprises at least one of a lignin monomer unit and a lignin oligomer thereof, the lignin monomer unit comprising an aromatic group with one or more substituents selected from the group consisting of alcohol groups, ether groups, aldehyde groups, ketone groups, alkyl groups, carboxyl groups, and combinations thereof.

Various refinements and embodiments of the methods for depolymerizing lignin are possible.

In a refinement, the lignin compound comprises a cross-linked phenolic polymer comprising at least one of β-O-4 ether linkages, α-O-4 ether linkages, 4-O-5 ether linkages, β-β carbon-carbon linkages, β-1 carbon-carbon linkages, β-5 carbon-carbon linkages, and 5-5 carbon-carbon linkages between phenolic monomer units in the cross-linked phenolic polymer. The lignin compound can be in any desired form and from any desired biomass or lignocellulosic feed stock, for example as an isolated lignin material or a lignocellulosic material in combination with cellulose and/or hemicellulose. In a further refinement, the lignin compound is at least partially oxidized to include lignin ketone groups in place of native lignin alcohol groups. The lignin compound can be an untreated lignin or it can be mechanically and/or chemically pre-treated prior to depolymerization with thiols. In an embodiment, the lignin compound is pretreated prior to being depolymerized with thiols according to the disclosure, for example being pretreated with a copper-catalyzed alkaline hydrogen peroxide (Cu-AHP) pretreatment or other pretreatments that at least partially oxidize lignin alcohol groups to ketone groups. The lignin compound can include any or all of its original carbon-oxygen-carbon ether linkages and/or carbon-carbon linkages, or it can contain a subset thereof if it has been pretreated. In a further refinement, the depolymerized lignin product has 50% or less, or 60% or less, linkages between phenolic monomer units in the cross-linked phenolic polymer relative to the lignin compound prior to reacting (e.g., at least 1, 2, 5, 10, or 20% and/or up to 5, 10, 15, 20, 30, 40, 50, or 60% of linkages, which can be expressed relative to all types of linkages in the starting material or a particular type of the foregoing linkages in the starting material.) For example, in some refinements, the β-O-4 ether linkages are cleaved (e.g., in particular where the alcohol on the alpha carbon has been oxidized to a ketone such as in a lignin pretreatment process) in the depolymerized lignin product and are reduced relative to the lignin compound prior to reacting (e.g., at least 1, 2, 5, 10, or 20% and/or up to 5, 10, 15, 20, 30, 40, 50, or 60% β-O-4 ether linkages in the depolymerized lignin product relative to those in the lignin compound prior to reacting).

In another refinement, the depolymerized lignin product has a molecular weight of 60% or less relative to the molecular weight of the lignin compound prior to reacting. For example, the depolymerized lignin product can have a molecular weight of at least 1, 2, 5, 10, or 20% and/or up to 5, 10, 15, 20, 30, 40, 50, or 60% relative to the lignin compound starting material. Relative molecular weight reduction by depolymerization can be expressed on any suitable molecular weight basis, for example number-average molecular weight or weight-average molecular weight.

In another refinement, the lignin compound prior to reacting has a number-average molecular weight of at least 400 g/mol (e.g., at least 400, 1000, 2000, 5000, or 10000 g/mol and/or up to 2000, 5000, 10000, 20000, or 50000 g/mol). In a further refinement, the depolymerized lignin product has a number-average molecular weight of 50% or less, or 60% or less, relative to the number-average molecular weight of the lignin compound prior to reacting (e.g., at least 1, 2, 5, 10, or 20% and/or up to 5, 10, 15, 20, 30, 40, 50, or 60% number-average molecular weight of the depolymerized lignin product relative to the lignin compound starting material).

In another refinement, the lignin compound prior to reacting has a weight-average molecular weight of at least 10000 g/mol (e.g., at least 10000, 20000, 30000, 40000, or 50000 g/mol and/or up to 20000, 50000, 100000, 200000, or 500000 g/mol). In a further refinement, the depolymerized lignin product has a weight-average molecular weight of 50% or less, or 60% or less, relative to the weight-average molecular weight of the lignin compound prior to reacting (e.g., at least 1, 2, 5, 10, or 20% and/or up to 5, 10, 15, 20, 30, 40, 50, or 60% weight-average molecular weight of the depolymerized lignin product relative to the lignin compound starting material).

In another refinement, the depolymerized lignin product comprises at least one of a lignin monomer unit and a lignin oligomer thereof, the lignin monomer unit comprising an aromatic group with one or more substituents selected from the group consisting of alcohol groups, ether groups, aldehyde groups, ketone groups, alkyl groups, carboxyl groups, and combinations thereof (e.g., a $C_6$ mono- or poly-substituted aromatic ring with substituents having 0, 1, 2, 3, 4, or 5 carbon atoms, such as where an alcohol (—OH) group contains 0 carbon atoms, while the other substituents contain at least 1 carbon atom). Lignin oligomers can have at least 2, 3, 5, or 10 and/or up to 10, 20, 30, or 50 monomer units. The depolymerized lignin product can include a plurality or distribution of different lignin monomer units and lignin oligomers with differing types and numbers of monomer units. In a further refinement, the lignin monomer unit is selected from the group consisting of phenol, cresol, guaiacol, 4-ethyl-guaiacol, eugenol, isoeugenol, methoxyeugenol, syringol, acetophenone, and combinations thereof (e.g., as mixture of monomers or different monomers in an oligomer). In a further refinement, the depolymerized lignin product is substantially free from adducts of the thiol compound with the lignin monomer unit or the lignin oligomer thereof. For example, the reaction can proceed such that intermediate adducts of the thiol compound with the lignin monomer unit or the lignin oligomer thereof formed during reaction are subsequently cleaved and are not present in the product reaction medium at substantial levels, such as not more than 0.1%, 1%, 2%, or 5% relative to the lignin content of the reaction system (e.g., relative to the starting lignin compound and/or the depolymerized lignin product as a whole).

In another refinement, the thiol compound comprises a monothiol compound (e.g., a thiol compound having only one —SH thiol group, such as benzenethiol and 2-mercaptoethanol. In a further refinement, only monothiol compounds are used and/or otherwise present in the reaction system.

In another refinement, the thiol compound comprises a dithiol compound (e.g., a thiol compound having only two —SH thiol groups, such as dithiothreitol (DTT) and 1,3-propanedithiol. In a further refinement, only dithiol compounds are used and/or otherwise present in the reaction system.

In another refinement, the thiol compound comprises a hydrocarbon group having 1 to 10 carbon atoms and being substituted with 1 to 4 thiol (—SH) groups. For example, the hydrocarbon group can be a linear or branched alkyl group or aromatic group, such as having at least 1, 2, 3, or 4 and/or up to 3, 4, 6, 8, or 10 carbon atoms, and being substituted with 1, 2, 3, or 4 thiol groups. The thiol compound optionally can be substituted with 1, 2, 3, or 4 hydroxyl (—OH) groups, amino (primary —$NH_2$ or secondary —NH—) groups, amide ((C=O)N) groups, urea (N(C=O)N) groups, and/or carboxylic (COOH) groups. In some refinements, the thiol groups and optionally the hydroxyl groups are the only functional groups in the thiol compound as substituents for the hydrocarbon group.

In another refinement, reacting the lignin compound with the thiol compound further comprises forming an oxidized thiol reaction product between two thiol groups from one or more thiol compounds. For example, the method can form a further reaction product containing a disulfide S—S bond between two thiol groups. The reaction product can be a dimer formed between two thiol compound molecules, for example two mono-thiol compound molecules. The reaction product also can be an intramolecular cyclic reaction product formed from a single thiol compound molecule with two or more original thiol groups. In a further refinement, the method further comprises reducing the oxidized thiol reaction product to re-form the thiol compound (e.g., regeneration of original thiol compound after oxidation so that the thiol compound can be used for further cleavage/depolymerization of lignin without addition of more thiol compound reactant). Further reduction can be suitably performed electrochemically (such as in situ with the reaction for lignin depolymerization), but can be performed by other suitable chemical reduction means.

In another refinement, the method comprises reacting the lignin compound with the thiol compound in a solvent reaction medium (e.g., a suitable solvent for the lignin compound, the thiol compound, and/or the depolymerized lignin product, for example in a homogeneous reaction system; electrochemical or other reduction to regenerate thiol compound can be similarly performed in the solvent reaction medium). In a further refinement, the solvent reaction medium comprises a solvent selected from the group consisting of tetrahydrofuran (THF), dimethylformamide (DMF), acetonitrile (ACN or MeCN), water, dioxane, dimethyl sulfoxide (DMSO), N-methyl-2-pyrrolidone (NMP), methanol (MeOH), γ-valerolactone (GVL), and combinations thereof (e.g., suitably a polar protic or aprotic solvent, other polar or non-polar organic solvents, lignin compounds, and/or depolymerized lignin products). In some refinements, the solvent reaction medium is free from water (e.g., free from added water, although some natural water content in the lignin compound from a biomass feedstock and/or residual water in a non-water solvent is possible).

In another refinement, the method comprises reacting the lignin compound with the thiol compound at a temperature ranging from 20° C. to 200° C. (e.g., at least 20° C., 25° C., 30° C., 50° C., 70° C., or 90° C. and/or up to 50° C., 80° C., 100° C., 120° C., 150° C., or 200° C., such as at or below the boiling point of any solvent medium). The reaction time in a batch reaction system or residence time in a continuous reaction system can be suitably selected to achieve a suitable conversion and/or yield. In a further refinement, reacting the lignin compound with the thiol compound can be performed at a pH value of at least 2, 3, 4, or 5 and/or up to 8, 9, 10, 11, or 12 (e.g., as pH value during reaction or at the end of reaction during a quench step).

While the disclosed compounds, methods, and compositions are susceptible of embodiments in various forms, specific embodiments of the disclosure are illustrated (and will hereafter be described) with the understanding that the disclosure is intended to be illustrative, and is not intended to limit the claims to the specific embodiments described and illustrated herein.

DETAILED DESCRIPTION

Provided herein are methods of depolymerizing lignin. In general, the methods of the disclosure include reacting a lignin compound with a thiol compound to depolymerize the lignin compound and to form a depolymerized lignin product having a reduced molecular weight relative to the lignin compound prior to reacting.

Figure 2:
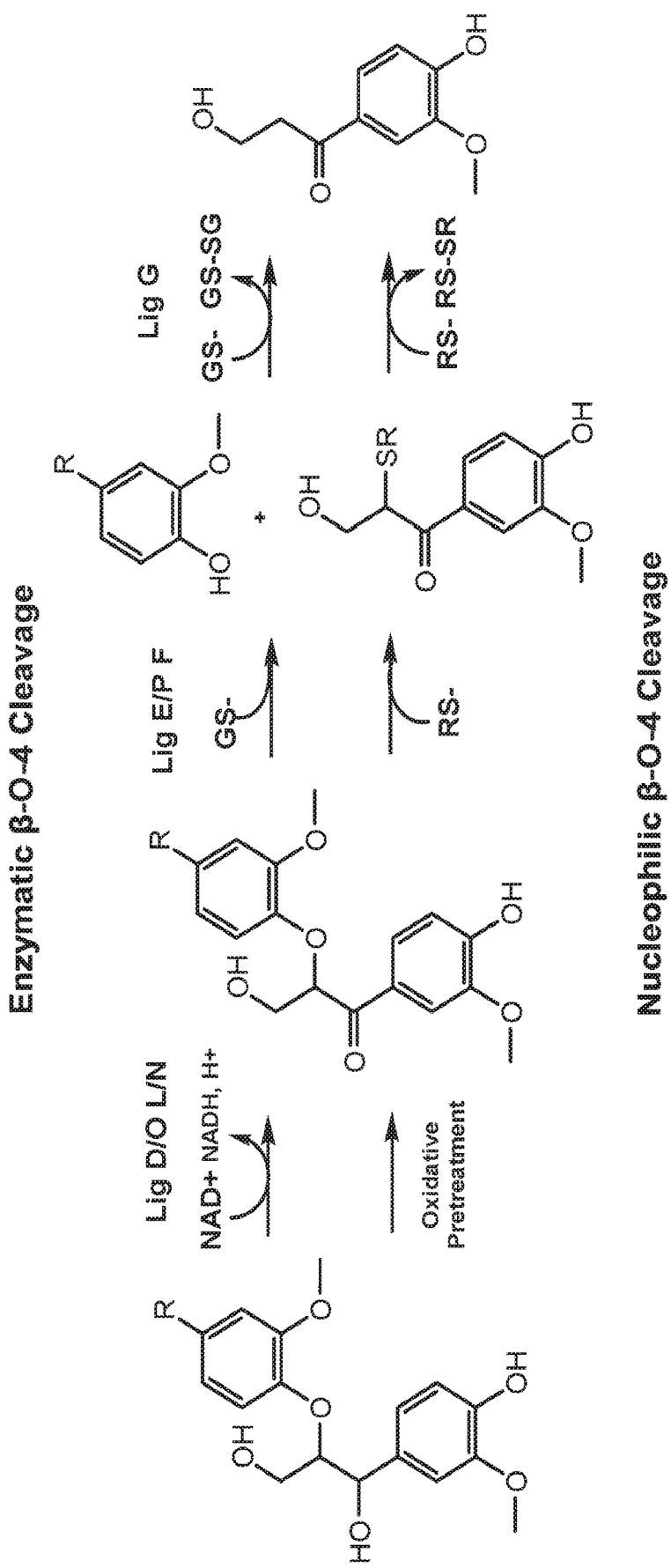
FIG. 2 shows the enzymatic β-etherase degradation pathway of a β-O-4 linkage (top) versus the biomimetic degradation of a β-O-4 linkage (bottom), according to a method of the disclosure.

A comparison of the biological mechanisms of β-aryl ether cleavage of lignin by fungi and a method according to the disclosure are shown in FIG. 2. The biological mechanism involves the oxidation of the hydroxy group in the α-position to a carbonyl using an NAD+ dependent stereoselective C-α-dehydrogenase, shown in FIG. 2 as Lig D, Lig O, Lig L, and Lig N. Stereospecific β-etherases cleave the β-O-4 linkage with the cofactor glutathione, shown in FIG. 2 as Lig E, Lig P, and Lig F. This is achieved via a nucleophilic attack on the β-carbon, releasing the phenolic subunit and yielding a glutathione adduct. The last step is the addition of a glutathione lyase that cleaves the glutathione lignin moiety to produce an oxidized glutathione dimer and the release of the second lignin subunit, shown in FIG. 2 as Lig G. This subunit is further metabolized to allow *Sphingobium* growth. In summary, Lig D, L, N, and O are the dehydrogenases, Lig E, F, and P are the β-etherases, and Lig G is the lyase.

Thiols, both mono- and di-, have been found to cleave the β-aryl ether bond of lignin and model systems thereof as a biomimetic route stemming from β-etherases from the glutathione S-transferase family. Advantageously, these thiols can cleave lignin under mild reaction conditions (e.g., temperature, solvent, etc.), and can be recycled and reformed for use in further lignin depolymerization reactions.

Lignin Compound

Plants, in general, are comprised of cellulose, hemicellulose, pectin, and lignin. Cellulose can be thought of as a crystalline glucose polymer. It is a six-carbon sugar that is a major structural component of cell walls. Hemicellulose is a mixture of five and six-carbon sugars with an amorphous structure that acts as a branching polymer that cross links around the cellulose. Pectin is a complex polysaccharide that helps bind the plant cells together. Lignin is an amorphous aromatic polymer that is made of methoxy substituted catechols. The more methoxy substitutions on the aromatic polymer, the easier the plant is to degrade. This is due to radical-generated cross linking between non-substituted positions on the ring making lignin a stronger polymer. Cellulose, hemicellulose, and lignin give the plant structural support. The linkages that dictate these interactions are important for the deconstruction of this feedstock. Intramolecular linkages include: hydrogen and ether bonds in cellulose; ester and ether bonds in hemicellulose; and carbon-carbon and ether bonds in lignin. Intermolecular linkages allow the lattice-like interaction and include: ether and hydrogen bonds between lignin and cellulose; ether, ester, and hydrogen bonds between lignin and hemicellulose; and hydrogen bonding between cellulose and hemicellulose. It is these stronger bonds with lignin that reduce the efficiency of lignocellulosic deconstruction.

Figure 1A:
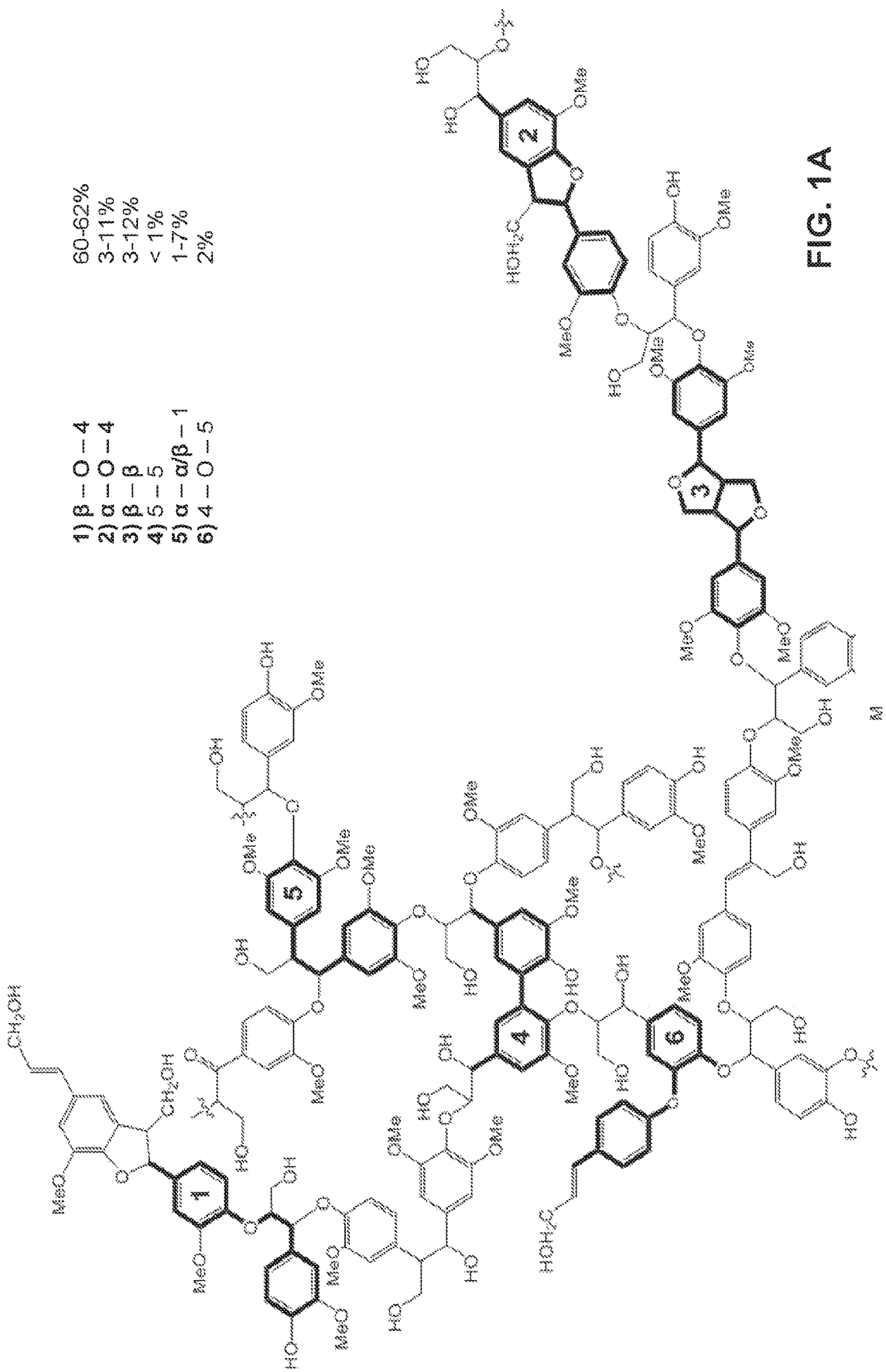
FIG. 1 illustrates chemical structures representative of lignin. Panel (A) illustrates a crosslinked lignin structure, with the indicated distribution of various bond types being representative of hardwoods. Panel (B) illustrates various linkages found in lignin.
Figure 1B:
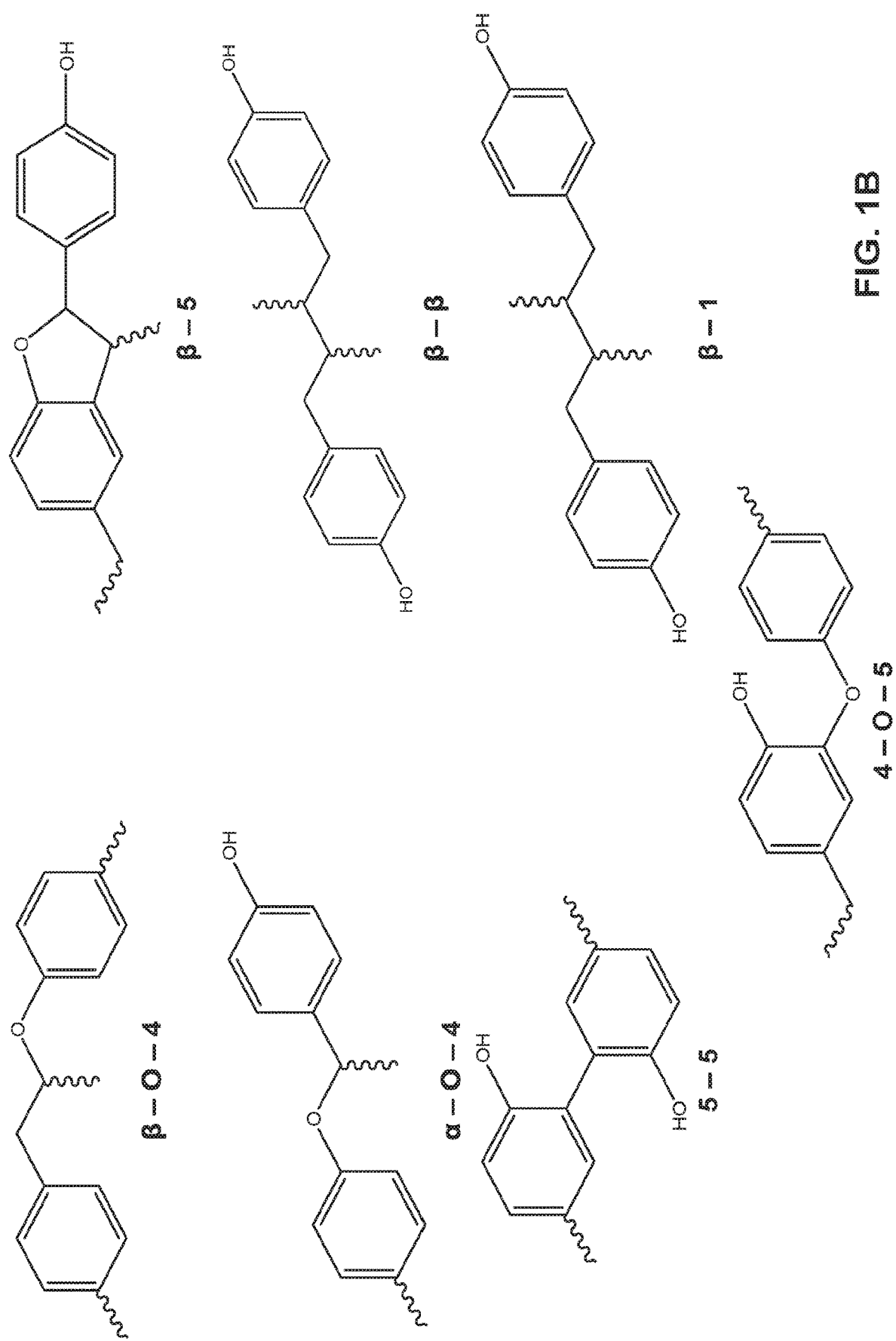

The ether bond is the predominant linkage in lignin, but various linkages make up this aromatic polymer, including: β-O-4, α-O-4, β-5, 4-O-5, 5-5, β-β, and β-1, with the percentage of each varying between numerous feedstocks. These linkages have their own naming system separate from the IUPAC nomenclature. To name these linkages, numbering the ring starts at the propyl unit, followed by numbering to the closest methoxy; from the propyl group, the Greek alphabet is counted out. For example, as shown in FIG. 1 (panel (B)), the β-1 linkage hydroxyl group is at position 4 and the 1 position is connected to the β-carbon of the propyl group from the other phenol, making a β-1 linkage.

In hybrid poplar, an important feedstock due to its fast growth and ability to grow on marginal lands, the β-O-4 bond is the major linkage, accounting for roughly 70% with the other five linkage types accounting for the remaining 30%. It is this β-aryl ether bond that has been the primary focus of lignin deconstruction.

The lignin compound depolymerized according to the methods of the disclosure is not particularly limited. The lignin compound can include a cross-linked phenolic polymer including at least one of (β-O-4 ether linkages, α-O-4 ether linkages, 4-O-5 ether linkages, β-β carbon-carbon linkages, β-1 carbon-carbon linkages, β-5 carbon-carbon linkages, and 5-5 carbon-carbon linkages between phenolic monomer units in the cross-linked phenolic polymer. In some embodiments, the lignin compound is characterized by at least 40%, 50%, or 60% and/or up to 60%, 70%, 75%, or 80% of its linkages as being (β-O-4 ether linkages.

Furthermore, the lignin compound can be in any desired form and from any desired biomass or lignocellulosic feedstock. For example, the lignin compound can be an isolated lignin material or a lignocellulosic material in combination with cellulose and/or hemicellulose. In embodiments, the lignin compound is at least partially oxidized to include lignin ketone groups in place of native lignin alcohol groups. The lignin compound can be an untreated lignin compound or it can be mechanically and/or chemically pre-treated prior to depolymerization with thiols. In an embodiment, the lignin compound is pretreated prior to being depolymerized with thiols according to the disclosure, for example being pretreated with a copper-catalyzed alkaline hydrogen peroxide (Cu-AHP) pretreatment, as disclosed in Example 3 herein. Other pretreatments that at least partially oxidize lignin alcohol groups to ketone groups are also suitable. In embodiments, the lignin compound includes any or all of its original carbon-oxygen-carbon ether linkages and/or carbon-carbon linkages. In embodiments wherein the lignin has been pretreated, the lignin can include a subset of its original carbon-oxygen-carbon ether linkages and/or carbon-carbon linkages.

The number-average molecular weight (Mn) of the lignin compound prior to reacting is not particularly limited. The number-average molecular weight of the lignin compound prior to reacting can be at least about 400 g/mol, about 1000 g/mol, 2000 g/mol, 5000 g/mol or about 10,000 g/mol, up to about 2000 g/mol, about 5000 g/mol, about 10,000 g/mol, about 20,000 g/mol, or about 50,000 g/mol. That is, the number-average molecular weight of the lignin compound prior to reacting can range from about 400 g/mol to about 50,000 g/mol, about 1000 g/mol to about 20,000 g/mol, about 2000 g/mol to about 10,000 g/mol, for example, about 400, 500, 600, 700, 800, 900, 1000, 1250, 1300, 1500, 1750, 2000, 2500, 3000, 3500, 4000, 4500, 5000, 5500, 6000, 6500, 7000, 7100, 7200, 7500, 8000, 8500, 9000, 10,000, 15,000, 20,000, 25,000, 30,000, 35,000, 40,000, 45,000 and 50,000 g/mol.

The weight-average molecular weight (Mw) of the lignin compound prior to reacting is not particularly limited. The weight-average molecular weight of the lignin compound prior to reacting can be at least about 10,000 g/mol, about 20,000 g/mol, about 30,000 g/mol, about 40,000 g/mol, or about 50,000 g/mol up to about 20,000 g/mol, about 50,000 g/mol, about 100,000 g/mol, about 200,000 g/mol, or about 500,000 g/mol. That is, the weight-average molecular weight of the lignin compound prior to reacting can range from about 10,000 g/mol to about 500,000 g/mol, about 20,000 g/mol to about 200,000 g/mol, about 30,000 g/mol to about 100,000 g/mol, or about 40,000 g/mol to about 50,000 g/mol, for example about 10,000, 11,000, 15,000, 20,000, 30,000, 40,000, 45,000, 46,000, 50,000 52,000, 55,000, 56,000, 60,000, 65,000, 70,000, 80,000, 90,000, 100,000, 125,000, 200,000, 250,000, 300,000, 350,000, 400,000, 450,000, and 500,000 g/mol.

Thiol Compound

The method according to the disclosure includes reacting the lignin compound with a thiol compound.

Sulfides and sulfites have been used for lignocellulosic degradation processing. For example, the pulp and paper industry has used several delignification methods involving sulfides. These methods include the Kraft process and the sulfite process. The Kraft pulping has been the dominant process in paper pulping and involves aqueous base and sodium sulfide, heated and pressurized, to cleave apart the intermolecular linkages of lignin, cellulose, and hemicellulose. This process allows the removal of lignin almost completely by sulfonating most of the hydroxy groups resulting in a low molecular weight lignin. However, the lignin resulting from this process includes extensive modifications that are unsuitable for conversion to liquid energy, in particular crosslinks added by the Kraft process that are harder to break than ether bonds as a liquid energy source. Sodium sulfite pulping involves the use of sulfite salts in acid to yield a nearly clean wood pulp of cellulose. However, this process does not lead to low molecular weight lignin like the Kraft process and instead produces lignosulfonates as byproducts. Furthermore, acidic solvolysis, namely, thioacidolysis, involves the addition of boron trifluoride etherate, a Lewis acid, and ethanethiol in dioxane for the acid-catalyzed β-aryl ether cleavage of lignin. Each of these processes have drawbacks, such as the use of expensive catalysts and/or toxic solvents, as well as unrealistic upscaling processes to effectively and efficiently break down lignin into simple aromatics for further chemical valorization.

In embodiments, the thiol compound can include a hydrocarbon group. As used herein, "hydrocarbon" refers to any straight-chained, branched, or cyclic group including or consisting of carbon and hydrogen, wherein the group can be saturated or unsaturated. In some embodiments, the thiol compound includes a hydrocarbon group having 1 to 10 carbon atoms, 1 to 8 carbon atoms, 2 to 6 carbon atoms, or 4 to 5 carbons, for example 1, 2, 3, 4, 5, 6, 7, 8, 9, or 10 carbon atoms. The hydrocarbon can be further substituted, wherein one or more of the hydrogen atoms has been replaced with a thiol, i.e., —SH, group. In embodiments, the hydrocarbon group can be substituted with 1 to 4 thiol groups, for example 1, 2, 3, or 4 thiol groups. The hydrocarbon can also be substituted with additional functional groups, such as, for example, hydroxyl groups, amino groups, aldehyde groups, ketone groups, carboxyl groups, ester groups, ether groups, amide groups, urea groups, ammonium groups, salts of the foregoing, and combinations thereof. In some embodiments, the thiol compound is substituted with 1, 2, 3, or 4 hydroxyl groups. In embodiments, the thiol group and hydroxyl groups are the only functional groups in the thiol compound as substituents for the hydrocarbon group.

In embodiments, the thiol compound includes a monothiol compound. As used herein, "monothiol" refers to any thiol compound having only one —SH thiol group. Examples of suitable monothiol compounds include, but are not limited to, β-mercaptoethanol, thiophenol (benzenethiol), 3-mercapto-1-propanol, 1-mercapto-2-propanol, 6-mercaptohexanol, 8-mercaptooctanol, 3-mercapto-3-methylbutanol, mercaptoacetic acid, mercaptopropionic acid, mercaptodecanoic acid, glutathione, and combinations of the foregoing. Examples of other suitable monothiol compounds include prop-2-ene-1-thiol, methyl-3-mercaptopropanoate, 3-nitrobenzenethiol, prop-1-ene-2-thiol, 2-mercaptopropanoate, ethanethiol, 1-(4-mercaptophenyl)ethane-1-one, methyl 2-mercaptoacetate, butane-1-thiol, cyclohexanethiol, ethyl 2-mercaptoacetate, pyridine-2-yl-methanethiol, (2-mercaptopropanoyl)glycine, propane-2-thiol, 3-methoxybenzenthiol, 2-ethoxyethane-1-thiol, cysteine, N-acetylcysteine, glutathione, 2-mercaptoacetic acid, phenylmethanethiol, 2-aminoethane-1-thiol, 3-mercaptopropanoic acid, 3-mercaptopropane-1,2-diol, 3-mercaptopropan-1-ol, 2-methylpropane-2-thiol, 2-methylbutane-2-thiol, 2-mercapto-2-methylpropan-1-ol, 4-chlorobenzethiol, and combinations thereof, including the foregoing monothiols. In embodiments, only monothiol compounds are used and/or otherwise present in the reaction system.

In embodiments, the thiol compound includes a dithiol compound. As used herein, "dithiol" refers to any thiol compound having only two —SH thiol groups. Examples of suitable dithiol compounds include, but are not limited to, dithiolthreitol, 1,3-propanedithiol, methanedithiol, 1,1-ethanedithiol, 1,1-cyclohexanedithiol, 1,2-ethanedithiol, benzenedithiol, and combinations of the foregoing. Examples of other suitable dithiol compounds include 1,2-dimercatopropan-2-ol, 2,3-dimercaptopropan-1-ol, 1,3-bis(2-mercaptoethyl)urea, ethane-1,2-dithiol, butane-1,4-dithiol, and combinations thereof, including the foregoing dithiols. In embodiments, only dithiol compounds are used and/or otherwise present in the reaction system. In embodiments, at least one dithiol compound and at least one monothiol compound are used and/or otherwise present in the reaction system.

Lignin Depolymerization Reaction

Glutathione S-transferase (GST), an enzymatic β-etherase, degrades lignin subunits via a nucleophilic attack of the cysteine sulfur of the glutathione cofactor on the β-aryl ether bond, releasing a phenoxide. Another glutathione-S-transferase protein then forms a protein dimer, enabling formation of a disulfide bond with another glutathione cysteine sulfur, thus releasing the second lignin monomer.

Following a biomimetic pathway, the method according to the disclosure includes reacting a lignin compound with a thiol compound to depolymerize the lignin compound and to form a depolymerized lignin product having a reduced molecular weight relative to the lignin compound prior to reacting.

The reaction conditions of the depolymerization reaction are not particularly limited. For example, in embodiments, the method includes reacting the lignin compound with the thiol compound under neat conditions. As used herein, "neat conditions" refer to reaction conditions in undiluted thiol that do not include a solvent. Neat conditions can include reacting the lignin compound with the thiol compound in the presence of an appropriate base, such as sodium carbonate or potassium carbonate. In some embodiments, reacting the lignin compound with the thiol compound can be carried out in a solvent reaction medium. The solvent reaction medium can include any solvent suitable to provide a homogeneous reaction system including the lignin compound, the thiol compound, and/or the depolymerized lignin product. Suitably, a polar protic or aprotic solvent miscible with water, other polar or non-polar organic solvents, lignin compounds, and/or depolymerized lignin products can be used. Examples of suitable solvents include, but are not limited to, tetrahydrofuran (THF), dimethylformamide (DMF), acetonitrile (ACN) (or methyl cyanide), water, dioxane, methanol, dimethyl sulfoxide (DMSO), N-methyl-2-pyrrolidone (NMP), γ-valerolactone (GVL), and combinations of the foregoing. In some embodiments, the solvent reaction medium is substantially free of water. As used herein, "substantially free of water" means that the reaction medium does not contain any intentionally or purposefully added water. Thus, incidental or background quantities of water may be present as natural water content in the lignin compound from a biomass feedstock and/or as a residual component of a non-water solvent is possible.

The temperature of the reaction medium is not particularly limited. In embodiments, the method includes reacting the lignin compound with the thiol compound at a temperature ranging from about 20° C. to about 200° C., about 25° C. to about 150° C., about 30° C. to about 120° C., about 50° C. to about 100° C., or about 70° C. to about 90° C., for example about 20, 25, 30, 35, 40, 50, 60, 70, 75, 80, 90, 100, 110, 120, 130, 140, 150, 160, 170, 180, 190, or 200° C. The reaction temperature is suitably chosen to be at or below the boiling point temperature of any solvent medium. The reaction time in a batch reaction system of residence time in a continuous reaction system can be suitably selected to achieve a suitable conversion and/or yield of the lignin depolymerization product. That is, reaction times may range from less than about 1 hour to at least about 48 hours. For example, reaction times can range from less than about 1 hour to about 48 hours, about 2 to about 40 hours, about 3 to about 36 hours, about 4 to about 38 hours, about 8 to about 30 hours, or about 10 to about 24 hours, for example about 1, 2, 3, 4, 5, 6, 7, 8, 12, 24, 36, or 48 hours.

The pH of the reaction medium is not particularly limited. In embodiments, reacting the lignin compound with the thiol compound can be carried out at a pH value ranging from at least about 2 to about 12, about 3 to about 11, about 4 to about 10, about 5 to about 9, or about 6 to about 8, for example, about 2, 3, 4, 5, 6, 7, 8, 9, 10, 11, or 12. The pH value as described herein can apply to the pH of the reaction medium during the reaction, or at the end of the reaction during a quenching step.

The method of disclosure provides a depolymerized lignin product.

In embodiments, the depolymerized lignin product has fewer linkages between phenolic monomer units in the cross-linked phenolic polymer relative to the lignin compound prior to reacting. The depolymerized lignin product can have about 50% or less, or 60% or less, linkages between phenolic monomer units in the cross-linked phenolic polymer relative to the lignin compound prior to reacting. For example, the depolymerized reaction product can have from less than about 1% to up to about 50% or 60%, less than about 2% to about 40%, less than about 5% to about 30%, or less than about 10% to about 20% linkages, for example about 1%, 2%, 5%, 10%, 15%, 20%, 25%, 30%, 35%, 40%, 45%, 50%, 55%, or 60% linkages between phenolic monomer units in the cross-linked phenolic polymer relative to the lignin compound prior to reacting.

The term "linkage," as used herein, can refer to all types of linkages in the starting material, for example, β-O-4, α-O-4, β-5, 4-O-5, 5-5, β-β, and/or β-1. Accordingly, the percentage of linkages remaining in the depolymerized lignin product can be expressed relative to all types of linkages in the starting lignin material. Similarly, the percentage of linkages remaining in the depolymerized lignin product can be expressed relative to a particular type of linkage in the starting lignin material. For example, in some embodiments, the β-O-4 ether linkages are cleaved in the depolymerized lignin product and are reduced relative to the lignin compound prior to reacting, providing a depolymerized lignin product having fewer β-O-4 ether linkages between phenolic monomer units in the cross-linked phenolic polymer relative to the lignin compound prior to reacting. That is, the depolymerized lignin product can have from about less than about 1% to up to about 50% or 60%, less than about 2% to about 40%, less than about 5% to about 30%, or less than about 10% to about 20% β-O-4 ether linkages, for example about 1%, 2%, 5%, 10%, 15%, 20%, 25%, 30%, 35%, 40%, 45%, 50%, 55%, or 60% β-O-4 ether linkages, relative to the starting lignin material.

In general, the depolymerized lignin product has a molecular weight less than that of the lignin compound prior to reacting. In embodiments, the depolymerized lignin product has a molecular weight of 50% or less, or 60% or less, relative to the molecular weight of the lignin compound prior to reacting. For example, the depolymerized lignin product can have a molecular weight from about 1% to about 50% or 60%, about 2% to about 40%, about 5% to about 30%, or about 10% to about 20%, for example about 1%, 2%, 5%, 10%, 15%, 20%, 25%, 30%, 35%, 40%, 45%, 50%, 55%, or 60% relative to the lignin compound prior to reacting. As used herein, relative molecular weight reduction by depolymerization can be expressed on any suitable molecular weight basis, such as, for example, number-average molecular weight, or weight-average molecular weight.

For example, in embodiments, the depolymerized lignin product has a number-average molecular weight of 50% or less, or 60% or less, relative to the number-average molecular weight of the lignin compound prior to reacting. That is, the depolymerized lignin product has a number-average molecular weight of from about 1% to about 50% or 60%, about 2% to about 40%, about 5% to about 30%, or about 10% to about 20%, for example about 1%, 2%, 5%, 10%, 15%, 20%, 25%, 30%, 35%, 40%, 45%, 50%, 55%, or 60%, relative to the number-average molecular weight of the lignin compound prior to reacting.

Similarly, in embodiments, the depolymerized lignin product has a weight-average molecular weight of 50% or less, or 60% or less, relative to the weight-average molecular weight of the lignin compound prior to reacting. That is, the depolymerized lignin product has a weight-average molecular weight of from about 1% to about 50% or 60%, about 2% to about 40%, about 5% to about 30%, or about 10% to about 20%, for example about 1%, 2%, 5%, 10%, 15%, 20%, 25%, 30%, 35%, 40%, 45%, 50%, 55%, or 60%, relative to the weight-average molecular weight of the lignin compound prior to reacting.

In embodiments, the depolymerized lignin product includes at least one of a lignin monomer unit and a lignin oligomer thereof, the lignin monomer unit including an aromatic group with one or more substituents. As used herein, "an aromatic group with one or more substituents" refers to a $C_6$ mono- or poly-substituted aromatic ring including substituents having 0, 1, 2, 3, 4, or 5 carbon atoms. The particular substituent on the aromatic ring is not particularly limited. For example, suitable substituents include, but are not limited to, alcohol groups, ether groups, aldehyde groups, ketone groups, alkyl groups, carboxyl groups, alkoxy groups, and combinations thereof. For example, a hydroxyl, —OH, substituent contains 0 carbon atoms, while other substituents, such as a ketone or an aldehyde group, contain at least 1 and up to 5 carbon atoms.

The lignin monomer is not particularly limited and can be selected from any monomer that is suitable to form a lignin oligomer or a lignin polymer. Examples of lignin monomers include, but are not limited to, phenol, cresol, guaiacol, 4-ethyl-guaiacol, eugenol, isoeugenol, methoxyeugenol, syringol, acetophenone, and combinations thereof. The lignin oligomer can include any suitable mixture or arrangement of lignin monomers.

The lignin oligomer can contain from about 2 to about 50 or 75 or 100, about 3 to about 30, about 5 to about 20, or about 10 to about 15 lignin monomer units, for example, about 2, 3, 5, 10, 15, 20, 25, 30, 35, 40, 45, 50, 75, or 100 lignin monomer units. The monomer units of the lignin oligomer are not particularly limited, and can include a plurality or distribution of different lignin monomer units and lignin oligomers with differing types and numbers of monomer units.

In embodiments, the depolymerized lignin product is substantially free from adducts of the thiol compound with the lignin monomer unit or the lignin oligomer thereof. That is, the depolymerized lignin product consists essentially of at least one of a lignin monomer unit and a lignin oligomer thereof. As used herein, the term "substantially free from adducts of the thiol compound" means the reaction can proceed such that the intermediate adducts of the thiol compound with the lignin monomer unit or the lignin oligomer thereof formed during reaction are subsequently cleaved and are not present in the product reaction medium at substantial levels, such as, for example, not more than 5%, not more than 2%, not more than 1%, or not more than 0.1% relative to the lignin content of the reaction system. The lignin content of the reaction system includes the starting lignin compound and/or the depolymerized lignin product(s), as a whole.

Reduction of Thiol Compound

In embodiments, the method includes forming an oxidized thiol reaction product between two thiol groups from one or more thiol compounds. For example, the reaction can include the formation of a disulfide S—S bond between two thiol groups with abstracted hydrogen atoms as a result of lignin cleavage. The oxidized thiol reaction product can be a dimer formed between two thiol compound molecules, for example, two monothiol compounds. The oxidized thiol reaction product can also be an intramolecular cyclic reaction product, formed from a single compound molecule having two or more thiol groups, such as dithiothreitol or other dithiol.

Advantageously, the method of the disclosure can allow for the recyclability of the sulfur, i.e. thiol, compounds. The recyclability of the thiol compound can be achieved, for example, using electrochemical means.

In order to utilize electrical energy for liquid fuel production, electrochemistry can be used. This process involves the reduction and/or oxidation of a substrate when an external voltage is applied. The method of the disclosure can include economically viable catalysts or electrodes for the depolymerization of lignin.

In embodiments, the method can include reducing the oxidized thiol reaction product to form the original thiol compound. That is, the oxidized thiol compound can be reduced and recycled to re-form the thiol compound used in the method according to the disclosure. Advantageously, the regeneration of the original thiol compound after being oxidized in the lignin depolymerization reaction allows the thiol compound to be used for further cleavage and/or depolymerization of lignin, without the addition of more thiol compound reactant. The reduction of the oxidized thiol compound can be suitably performed electrochemically in situ with the reaction for lignin depolymerization, but can also be performed using other suitable chemical reduction means.

Figure 7:
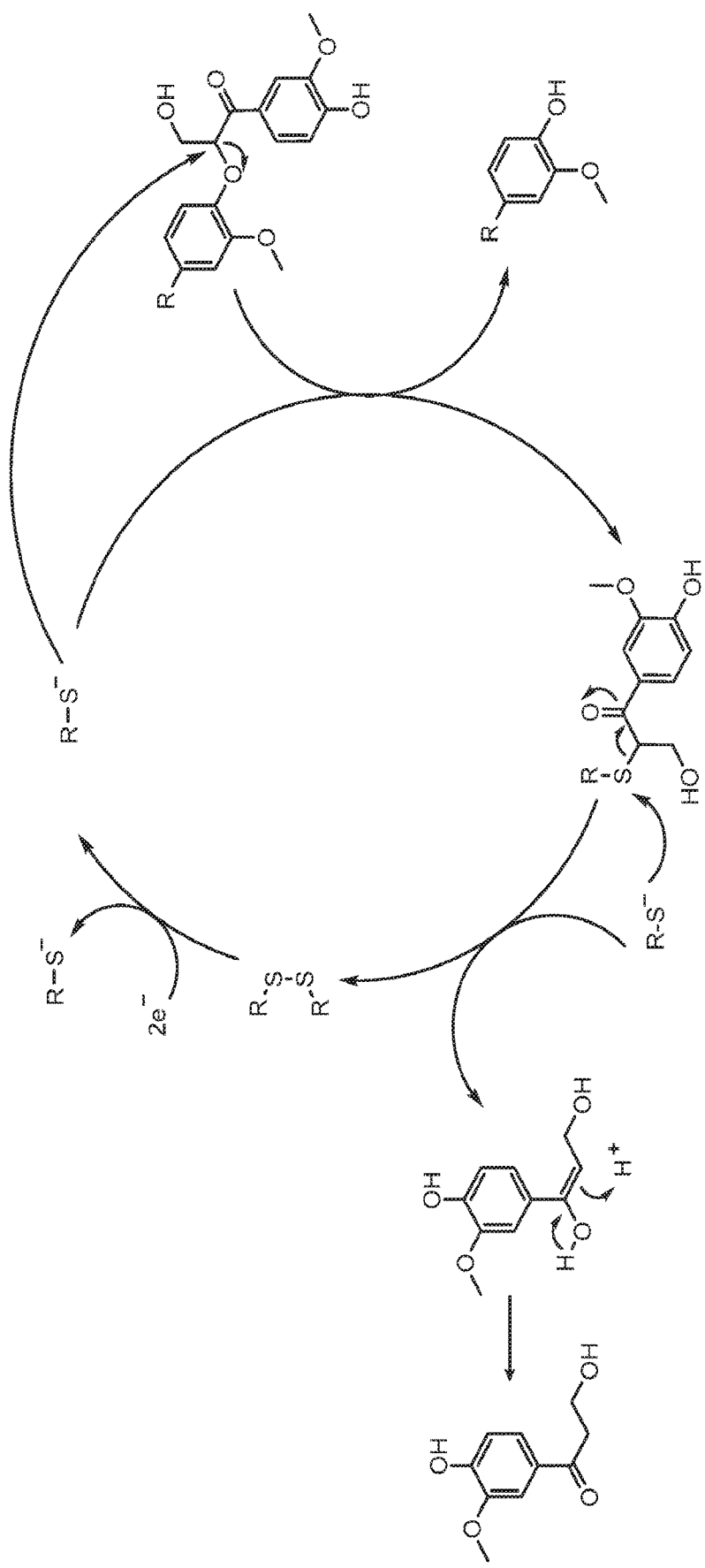
FIG. 7 shows a reaction cycle for an exemplary dithiol according to an embodiment of the disclosure.

The reaction cycle for an exemplary dithiol according to an embodiment of the disclosure is shown in FIG. 7. The scheme starts with the thiol group cleaving the β-O-4 bond, followed by the reaction of an additional thiol group (intramolecular reaction for dithiols, intermolecular reaction for monothiols) on the sulfur atom to form a disulfide bond. The oxidized thiol is then reduced in an electrochemical cell to obtain the original, starting thiol compound.

Because other modifications and changes varied to fit particular operating requirements and environments will be apparent to those skilled in the art, the disclosure is not considered limited to the example chosen for purposes of illustration, and covers all changes and modifications which do not constitute departures from the true spirit and scope of this disclosure.

Accordingly, the foregoing description is given for clearness of understanding only, and no unnecessary limitations should be understood therefrom, as modifications within the scope of the disclosure may be apparent to those having ordinary skill in the art.

All patents, patent applications, government publications, government regulations, and literature references cited in this specification are hereby incorporated herein by reference in their entirety. In case of conflict, the present description, including definitions, will control.

Throughout the specification, where the compounds, compositions, methods, and processes are described as including components, steps, or materials, it is contemplated that the compositions, processes, or apparatus can also comprise, consist essentially of, or consist of, any combination of the recited components or materials, unless described otherwise. Component concentrations can be expressed in terms of weight concentrations, unless specifically indicated otherwise. Combinations of components are contemplated to include homogeneous and/or heterogeneous mixtures, as would be understood by a person of ordinary skill in the art in view of the foregoing disclosure.

The above described aspects and embodiments can be better understood in light of the following examples, which are merely intended to be illustrative and are not meant to limit the scope in any way.

EXAMPLES

Reaction Protocol

The following protocol applies to Examples 1-4:

All chemicals were tested for purity using $^1$H NMR prior to use. Glutathione and DL dithiothreitol >99% were purchased from Gold Biotechnology (Olivette, Mo.); 2-phenoxyacetophenone >98% was purchased from TCI, Ltd; benzoin ethyl ether 97%, β-mercaptoethanol, 1,3-propanedithiol 99%, N—N-dimethylformamide 99.8% anhydrous, acetonitrile 99.5+%, trans-cinnamic acid, 4-phenoxyphenol 99%, 2-bromoacetophenone 98%, and 2,4'-dibromoacetophenone 98% were purchased from Sigma-Aldrich; thiophenol 99+%, and tetrahydrofuran (THF) 99+% with 250 ppm BHT were purchased from Alfa Aesar (Haverhill, Mass.); sodium carbonate 99.5% was purchased from Jade Scientific (Westland, Mich.); and dichloromethane was purchased from Macron. All water used was filtered using Thermo Scientific four-holder BARNSTEAD E-pure water purification 120 V systems. Lignin was precipitated from Cu-AHP pretreatment liquor and lyophilized into the form used.

All NMR spectra were taken using an Agilent DDR2 500 MHz NMR spectrometer equipped with 7600AS 96 sample autosampler and referenced to residual solvent peaks. HPLC analysis was performed using an Agilent 1260 INFINITY equipped with quaternary pump and a G1315D 1260 diode array detector VL, monitoring at 280 nm and recording 190-400 nm. For dimer and monomer analysis, a Supelco ASCENTIS EXPRESS C18 column 15 cm×4.6 cm, 2.7 µm was used in isocratic mode with a mobile phase of 0.4 ml/min 50:50 acetonitrile:water; 5 µL sample injections included phenanthrene as an internal standard; external standards were also rechecked during each sequence of analysis. Lignin analysis was performed using a Waters ULTRAHYDROGEL 250 7.8×300 mm GPC column in isocratic mode at 0.7 ml/min with a mobile phase of 0.005 M NaOH in 80/20 0.1 M aqueous sodium nitrate/acetonitrile; 50 µL injections included acetophenone as an internal standard; polystyrene sulfonic acid external standards were also run during each sequence. Instrumental control, data acquisition, and data processing for the HPLC were performed with Agilent CHEMSTATION. UV-vis spectra used for oxidation/reduction cycling were obtained with a Hewlett-Packard 8453. GCMS data used to analyze chemical purity were obtained with Agilent 5975b single quadrupole MS with a 6890 Agilent GC using an Agilent VF-5 ms 30m×0.25 mm×0.25 um+10m EZ-GUARD column.

A typical reaction setup included degassing and drying all solvent with sonication while sparging with nitrogen in the presence of 3 Å molecular sieves previously activated at 310° C. Reactions still proceed in the presence of air and without drying solvents. Sodium carbonate was baked at 130° C. and all glassware used was baked and degassed with nitrogen. All refluxing reactions were performed under nitrogen and heated in a temperature-calibrated sand bath.

Thioethers used to verify the reaction path were prepared at room temperature in air with approximately a 1:2 mole ratio of thiol to brominated monomer for approximately 24 hrs stirring with excess sodium carbonate. The reaction was then filtered and extracted with water and dichloromethane, then evaporated and purged under nitrogen overnight. NMR spectra were taken of samples dissolved in deuterated dimethyl sulfoxide (DMSO-$d_6$). Thioethers were also synthesized as follows: 2-Bromoacetophenone species (500 mg) was added to a mixture of triethylamine (280 mg, 2.76 mM) and thiol (196 mg, 2.51 mM) in $CH_2Cl_2$ (8 mL). The mixture was stirred at room temperature for 30 minutes. The solution was diluted with $CH_2Cl_2$ (60 mL) and extracted with 3×100 mL of deionized water. The organic layer was dried with sodium sulfate, concentrated, and purified by column chromatography with $CH_2Cl_2$/MeOH (95:5) or hexanes/EtOAc (50:50) resulting in an oil.

Reactions of thiols with lignin models were performed at or below refluxing conditions under nitrogen in a 1:1, 1:2, 1:10, 1:100, or neat mole ratio of lignin model to thiol and heated for approximately 24 hours stirring with sodium or potassium carbonate. Reactions were worked up either by (1) quenching with water, extracting with dichloromethane, evaporating, followed by purging with $N_2$ overnight to ensure solvent evaporation for NMR determination using DMSO-d6, or (2) sampled overtime and run directly on an HPLC equipped with a C18 column.

Neat reactions were run at 100-130° C., stirring with sodium or potassium carbonate for 24 hours in an approximately 1:300 mole ratio of lignin model to thiol. Reactions were either micro-centrifuged and the supernatant was added dropwise into DMSO-$d_6$ for NMR analysis or the samples were solubilized in water and either run directly on an HPLC equipped with a C18 column or extracted with dichloromethane and run on a GCMS.

GPC analysis was performed using 5 mg/mL sample concentration with an instrument flow rate of 0.7 mL/min, a run time of 40 minutes, and an injection volume of 50 µl at a column temperature of 40° C. Eluent used was 80:20 0.1 M sodium nitrate/acetonitrile with polystyrene sulfonic acid external standards of 1600, 5240, 7420, 16100, 33600, 71200, 88700 g/mol and acetophenone as an internal standard.

Example 1: Preparation of Thioethers 2-((2,3-di hydroxy-4-mercaptobutyl)thio)-1-phenylethan-1-one

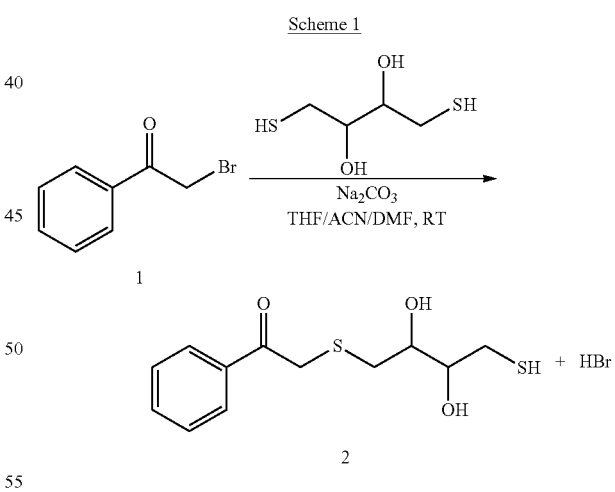

Scheme 1

2-Bromoacetophenone 1 (100 mg, 0.5 mmol) was added to 10 mL of an organic solvent of THF, ACN, or DMF with excess sodium carbonate. Dithiothreitol (100 mg, 0.648 mmol) was added slowly and the reaction was stirred at room temperature overnight. Reactions were filtered and quenched with equal volumes of MILLI-Q water and extracted with equal volumes of dichloromethane. The organic layer was extracted again with equal volumes of water and evaporated to form the product 2. $^1$H NMR (500 MHz, DMSO-$d_6$) δ 7.98 (d, J=7.7 Hz, 2H), 7.71-7.59 (m, 1H), 7.52 (t, J=7.8 Hz, 2H), 4.03 (s, J=6.8 Hz, 2H).

1-phenyl-2-(phenylthio)ethan-1-one 2-((3-mercaptopropyl)thio)-1-phenylethan-1-one

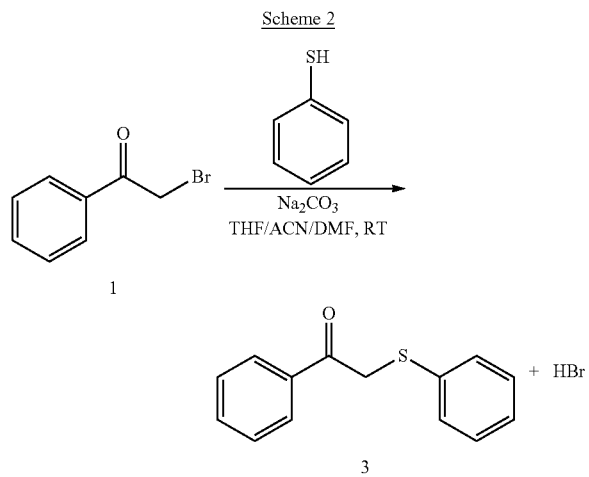

Scheme 2

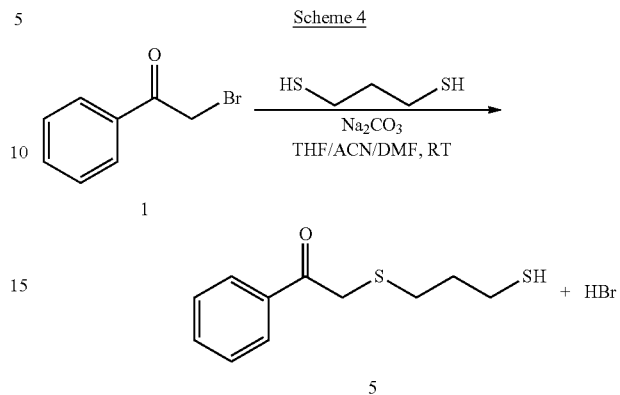

Scheme 4

2-Bromoacetophenone 1 (100 mg, 0.5 mmol) was added to 10 mL of an organic solvent of THF, ACN, or DMF with excess sodium carbonate. Thiophenol (100 mg, 0.9 mmol) was added slowly and the reaction was stirred at room temperature overnight. Reactions were filtered and quenched with equal volumes of MILLI-Q water and extracted with equal volumes of dichloromethane. The organic layer was extracted again with equal volumes of water and evaporated to form the product 3. $^1$H NMR (500 MHz, DMSO-$d_6$) (δ 8.03 (d, J=8.3 Hz, 2H), 7.76 (t, J=7.6 Hz, 1H), 7.57-7.47 (m, 4H), 4.67 (s, 2H).

2-((2-hydroxyethyl)thio-1-phenylethan-1-one

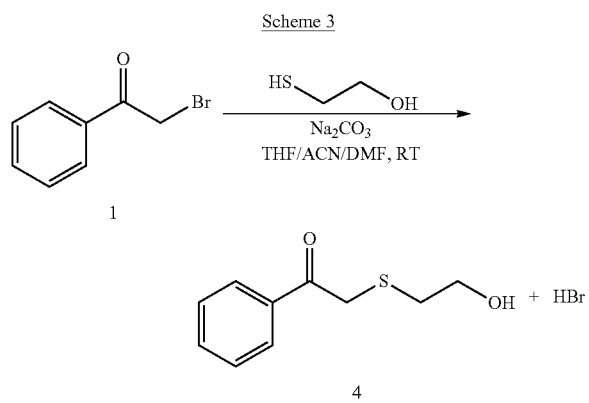

Scheme 3

2-Bromoacetophenone 1 (100 mg, 0.5 mmol) was added to 10 mL of an organic solvent of THF, ACN, or DMF with excess sodium carbonate. β-mercaptoethanol (100 mg, 1.3 mmol) was added slowly and the reaction was stirred at room temperature overnight. Reactions were filtered and quenched with equal volumes of MILLI-Q water and extracted with equal volumes of dichloromethane. The organic layer was extracted again with equal volumes of water and evaporated to form the product 4. $^1$H NMR (500 MHz, DMSO-$d_6$) (δ 7.97 (d, J=8.7 Hz, 2H), 7.62 (t, J=7.4 Hz, 1H), 7.50 (t, J=7.9 Hz, 2H), 4.01 (s, 2H).

2-Bromoacetophenone 1 (100 mg, 0.5 mmol) was added to 10 mL of an organic solvent of THF, ACN, or DMF with excess sodium carbonate. 1,3-propanedithiol (100 mg, 0.9 mmol) was added slowly and the reaction was stirred at room temperature overnight. Reactions were filtered and quenched with equal volumes of MILLI-Q water and extracted with equal volumes of dichloromethane. The organic layer was extracted again with equal volumes of water and evaporated to form the product 5. $^1$H NMR (500 MHz, DMSO-$d_6$) δ 7.96 (d, J=7.9 Hz, 2H), 7.64 (t, J=7.3 Hz, 1H), 7.53 (t, J=7.7 Hz, 2H), 4.00 (s, 2H).

Thus, Example 1 demonstrates the synthesis and NMR characterization of expected thioether intermediates. These reactions allowed for the identification of thioether intermediate(s) in the desired cleaved product by identifying the characteristic NMR and HPLC spectrum for each compound. More specifically, synthesis of the thioethers allows demonstrated the second half of the proposed cleavage reaction by identifying and quantifying the thioether intermediate via NMR and HPLC, and by specifically demonstrating that the thioether is quickly cleaved in the presence of additional thiol.

Example 2: Thiol Mediated Cleavage of 2-phenoxyacetophenone

Utilizing a biomimetic approach, 2-phenoxyacetophenone, the simplest oxidized β-O-4 dimer, was used as a model to probe β-O-4 cleavage using dithiol (i.e. dithiothreitol, and 1,3-propandithiol) and thiol (i.e. thiophenol and β-mercaptoethanol) mediators.

Dithiotreitol Cleavage of 2-phenoxyacetophenone

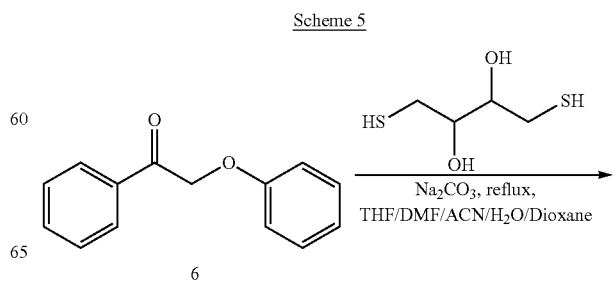

Scheme 5

-continued

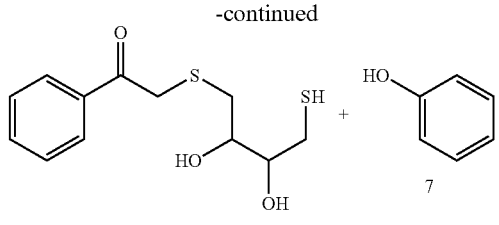

2

2-phenoxyacetophenone 6 (8 mg, 0.038 mmol) was added to excess sodium carbonate and dithiothreitol (0.058 g, 0.38 mmol) and purged under nitrogen. A 10 mL aliquot of dried and/or oxygen free solvent either THF, DMF, ACN, water, or dioxane was added through a septum. The reaction was refluxed under nitrogen overnight. It was then filtered, quenched with equal volumes of water, and extracted with equal volumes of dichloromethane. The organic layer was extracted again with equal volumes of water and evaporated to form the product 2, 7, 8. $^1$H NMR (500 MHz, DMSO-$d_6$) δ 7.97 (d, J=8.0 Hz, 2H), 7.65 (t, J=7.95 Hz, 1H), 7.54 (t, J=7.8 Hz, 2H), 7.16 (t, J=7.9 Hz, 2H), 6.80-6.72 (m, 3H).

Thiophenol Cleavage of 2-phenoxycetophenone

Scheme 6

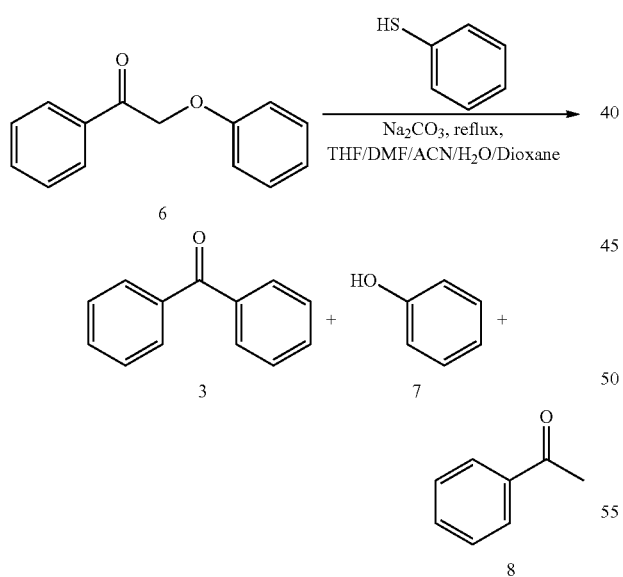

2-phenoxyacetophenone 6 (8 mg, 0.038 mmol) was added to excess sodium carbonate and purged under nitrogen. A 10 mL aliquot of dried and/or oxygen free solvent of either THF, DMF, ACN, water, or dioxane was added through a septum. Slowly, thiophenol (38.4 μL, 0.042 g, 0.38 mmol) was added through the septum and the reaction was refluxed under nitrogen overnight. It was then filtered, quenched with equal volumes of water, and extracted with equal volumes of dichloromethane. The organic layer was extracted again with equal volumes of water and evaporated to form the product 3, 7, 8. $^1$H NMR (500 MHz, DMSO-$d_6$) δ 7.96 (d, J=8.8 Hz, 2H), 6.75 (t, J=8.6 Hz, 3H), 4.67 (s, 2H).

β-mercaptoethanol Cleavage of 2-phenoxyacetophenone

Scheme 7

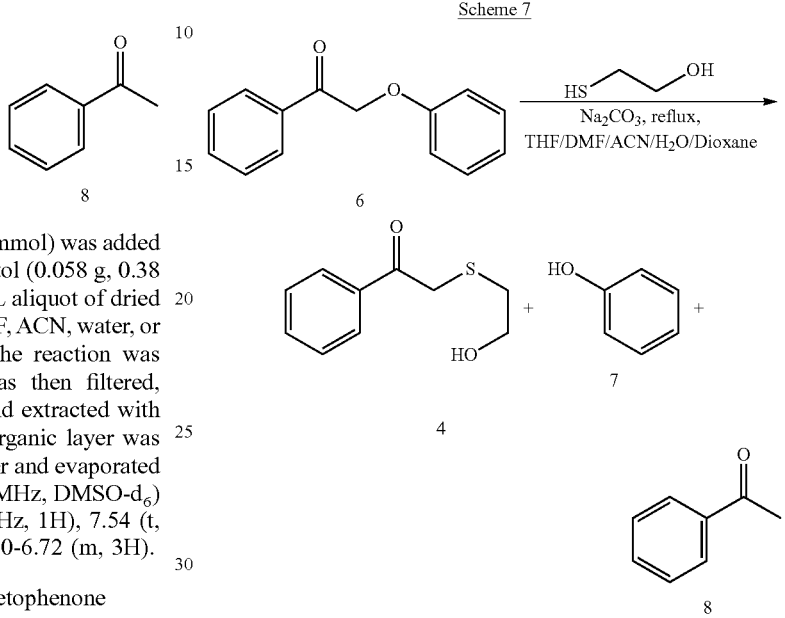

2-phenoxyacetophenone 6 (8 mg, 0.038 mmol) was added to excess sodium carbonate and purged under nitrogen. A 10 mL aliquot of dried and/or oxygen free solvent of either THF, DMF, ACN, water, or dioxane was added through a septum. Slowly, β-mercaptoethanol (26.5 μL, 0.03 g, 0.38 mmol) was added through the septum and the reaction was refluxed under nitrogen overnight. It was then filtered, quenched with equal volumes of water, and extracted with equal volumes of dichloromethane. The organic layer was extracted again with equal volumes of water and evaporated to form the product 4, 7, 8. NMR (500 MHz, DMSO-$d_6$) δ 7.97 (d, 2H), 7.64 (t, J=7.4 Hz, 1H), 7.53 (t, J=8.2 Hz, 2H), 7.28 (t, J=8.6 Hz, 2H), 6.75 (m, 3H), 4.02 (s, 2H).

1,3-propanedithiol Cleavage of 2-phenoxyacetophenone

Scheme 8

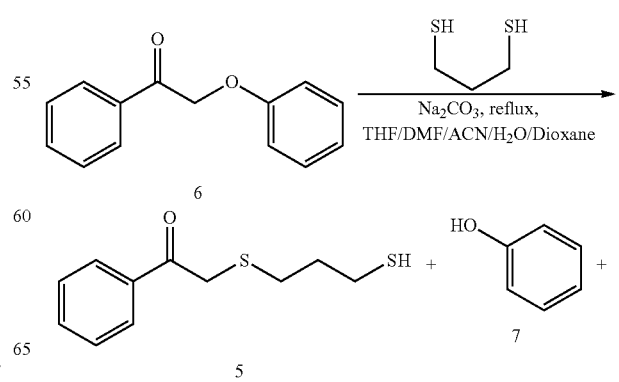

21
-continued

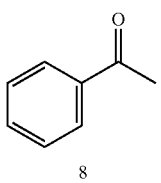

8

2-phenoxyacetophenone 6 (8 mg, 0.038 mmol) was added to excess sodium carbonate and purged under nitrogen. A 10 mL aliquot of dried and/or oxygen free solvent of either THF, DMF, ACN, water, or dioxane was added through a septum. Slowly, 1,3-propanedithiol (37.8 μL, 0.04 g, 0.38 mmol) was added through the septum and the reaction was refluxed under nitrogen overnight. It was then filtered, quenched with equal volumes of water, and extracted with equal volumes of dichloromethane. The organic layer was extracted again with equal volumes of water and evaporated to form the product 5, 7, 8. $^1$H NMR (500 MHz, DMSO-$d_6$) δ 7.96 (d, J=7.0 Hz, 2H), 7.64 (t, 1=7.4 Hz, 1H), 7.53 (t, J=7.7 Hz, 2H), 7.15 (t, J=8.65 Hz 2H), 6.75 (t, J=8.5 Hz, 3H).

The product ratios for the reactions described above using a DMF solvent are shown in Table 1, below.

22

As demonstrated in Table 1, thiol nucleophilic attack occurs at the β carbon of the β-O-4 linkage. Both monomers (i.e. phenol and acetophenone) released from the cleavage of the β-O-4 dimer model are seen in reactions with dithiothreitol and β-mercaptoethanol in DMF, but not thiophenol and 1,3-propanedithiol.

The results in Table 1 further show that β-mercaptoethanol can cleave the lignin model dimer with an 87.5% product conversion in DMF, while thiophenol only yielded trace amounts of the thioether. Thiophenol was chosen as a mediator to determine if the low yields in the conversion using the straight chain thiols were due to steric hinderance. The results, however, indicate this is not the case, due to meager thiophenol results.

The oxidized species (i.e., 2-phenoxyacetophenone) was found under inert reactions for all tested thiols.

The product ratios for the reactions described above under neat conditions are shown in Table 2, below.

TABLE 1

Product ratio of 2-phenoxyacetophenone from thiol reaction

| Thiol | starting material | thioether | phenol | acetophenone |
|---|---|---|---|---|
| dithiothreitol (HS-CH(OH)-CH(OH)-CH2-SH) | 88 | 0 | 8 | 4 |
| thiophenol | 99.9 | 0.1 | 0 | 0 |
| β-mercaptoethanol (HS-CH2-CH2-OH) | 10 / 99.5[a] / 97[b] | 3 / 0.5[a] / 3[b] | 68 / 0[a] / 0[b] | 19 / 0[a] / 0[b] |
| 1,3-propanedithiol | 100 | 0 | 0 | 0 |

Experiment done under inert conditions in DMF unless otherwise noted.
[a] = THF,
[b] = ACN

TABLE 2

Product ratio of 2-phenoxyacetophenone in solvent-free thiol reaction

| Thiol | (dimer) | (thioether) | (phenol) | (acetophenone) |
|---|---|---|---|---|
| HS-CH2-CH(OH)-CH(OH)-CH2-SH (dithiothreitol) | 0 | 0 | 73 | 27 |
| PhSH (thiophenol) | 70 | 9 | 14 | 7 |
| HS-CH2CH2-OH (β-mercaptoethanol) | 0 | 0 | 52 | 48 |
| HS-CH2CH2CH2-SH (1,3-propanedithiol) | 72 | 0 | 15 | 13 |

As demonstrated in Table 2, neat reactions with 2-phenoxyacetophenone in the presence of air show higher conversion. Dithiothreitol gave 100% product conversion while 1,3-propanedithiol yielded 28% product conversion. The β-mercaptoethanol reaction similarly gave complete conversion of the 2-phenoxyacetophenone while the thiophenol gave partial conversions of 30% product conversion including the unreacted thioether intermediate. Without intending to be bound by theory, this may be due to the decreased ability of the aromatic thiol to form a disulfide bond with a sterically hindered thioether dimer, yielding only phenol release as the major product.

Glutathione was also tested as a reducing mediator, and it was found spectroscopically through HPLC-GPC and NMR that this tripeptide gives moderate phenol yields, demonstrating the first half of the cleavage pathway. However, production of acetophenone was not observed, suggesting that the second half of the cleavage pathway did not occur to a large extent.

Figure 3B:
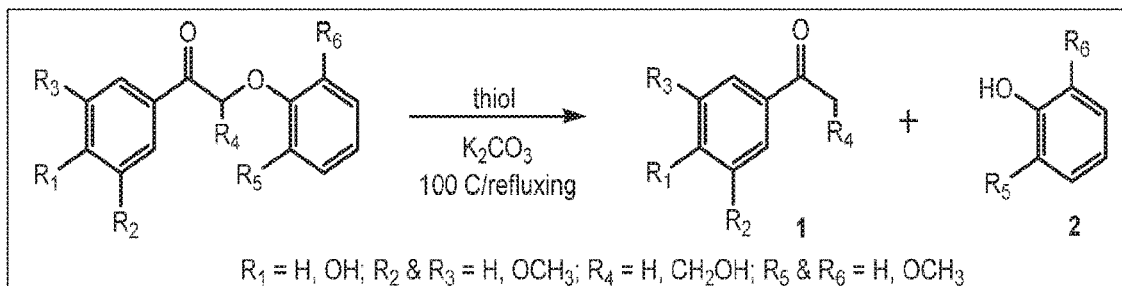
FIG. 3 shows the cleavage of 2-phenoxyacetophenone using various thiols, solvents, mole ratios, temperatures, and reaction times. The table shows a summary of dimer cleavage yields using differing thiols, solvents, mole ratios, and temperatures, at the highest conversion in the least amount of time. An asterisk (*) indicates that the reaction occurs immediately under refluxing conditions and that substrate starting concentration is skewed due to fast reaction. Panel (B) shows a continuation of the data from panel (A).
Figure 4A:
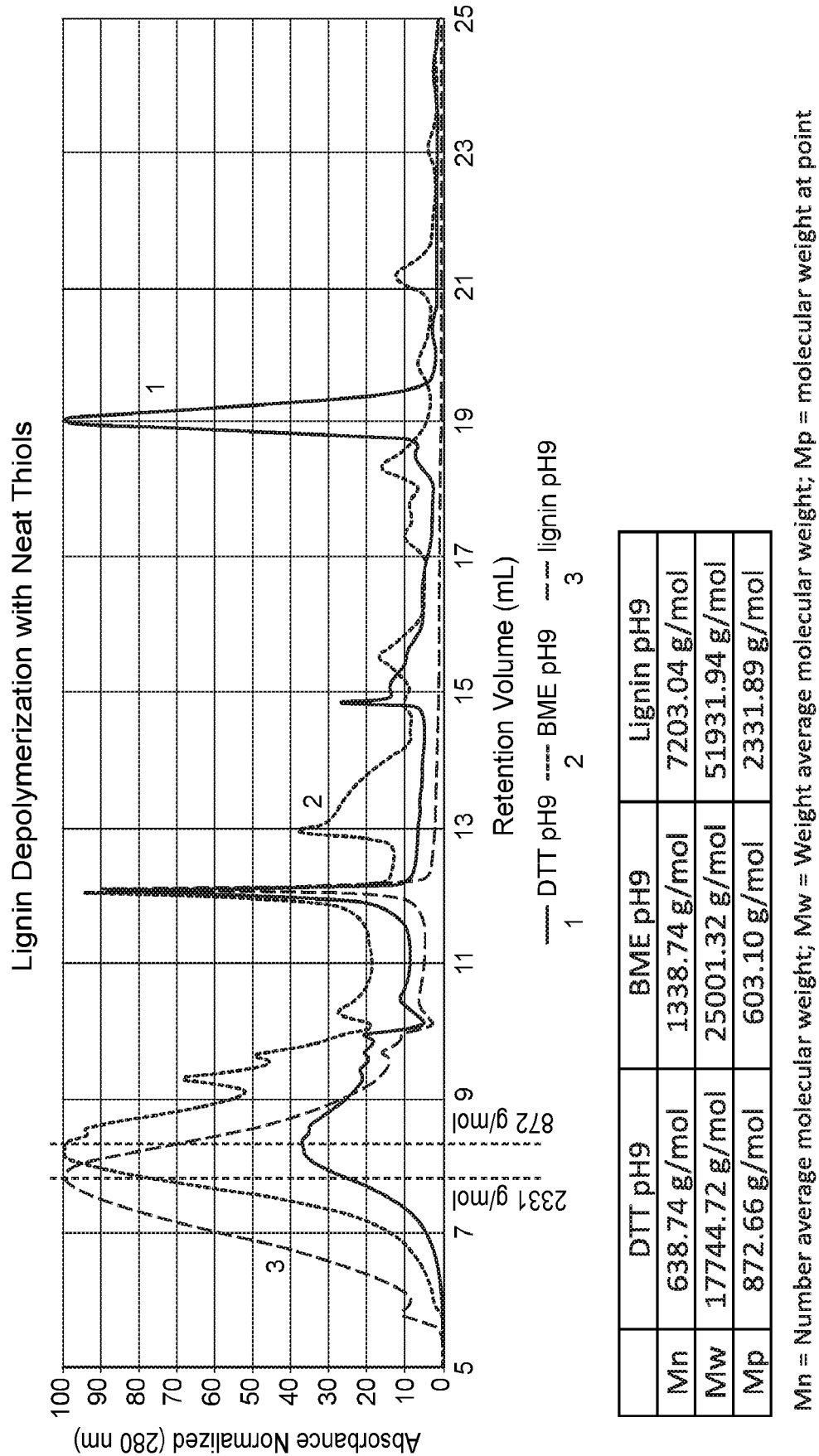
FIG. 4 shows a GPC spectrum of the reaction products of a lignin depolymerization reaction carried out under neat conditions and quenched at pH 9 (panel (A)), pH 7 (panel (B)), pH 2 (panel (C)), and pH 9 (panel (D)).
Figure 4B:
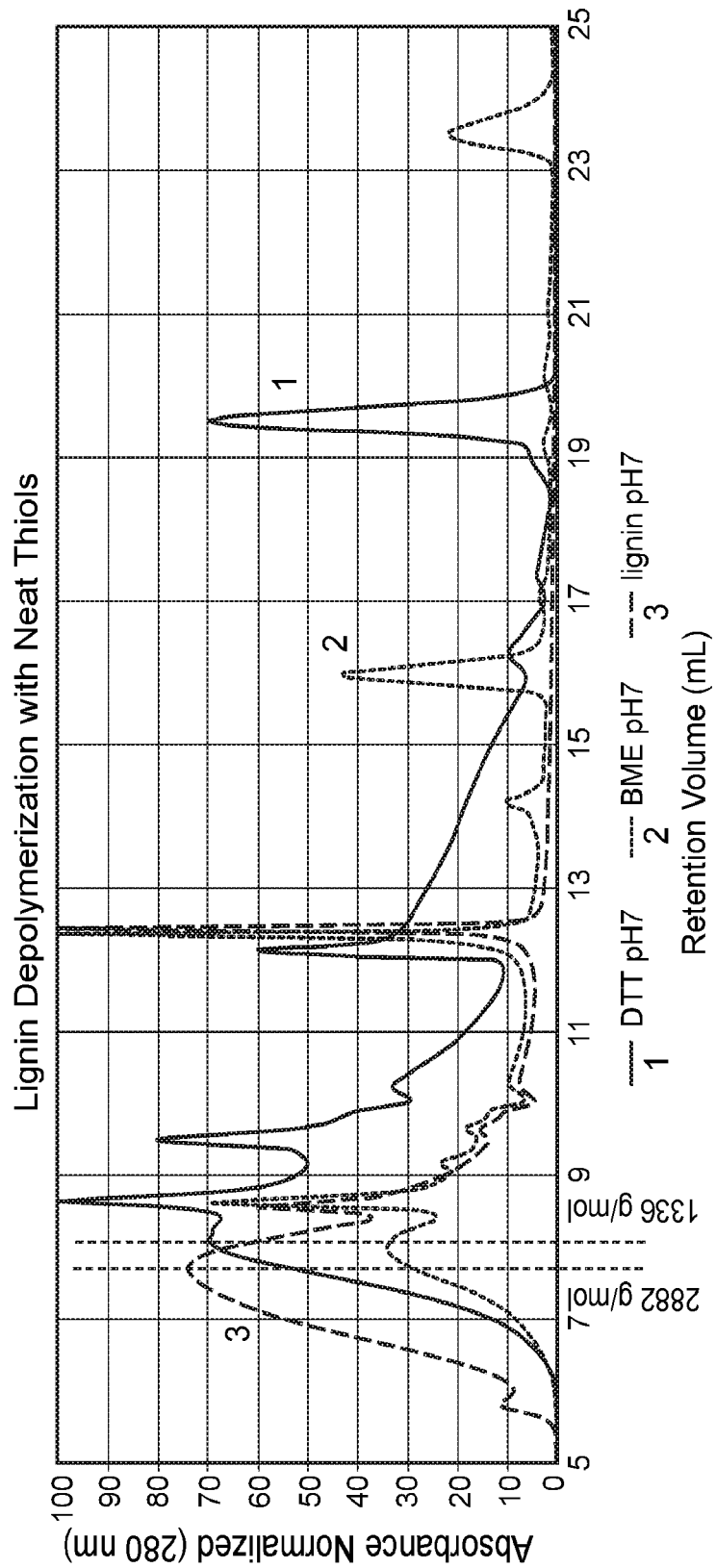
Figure 4C:
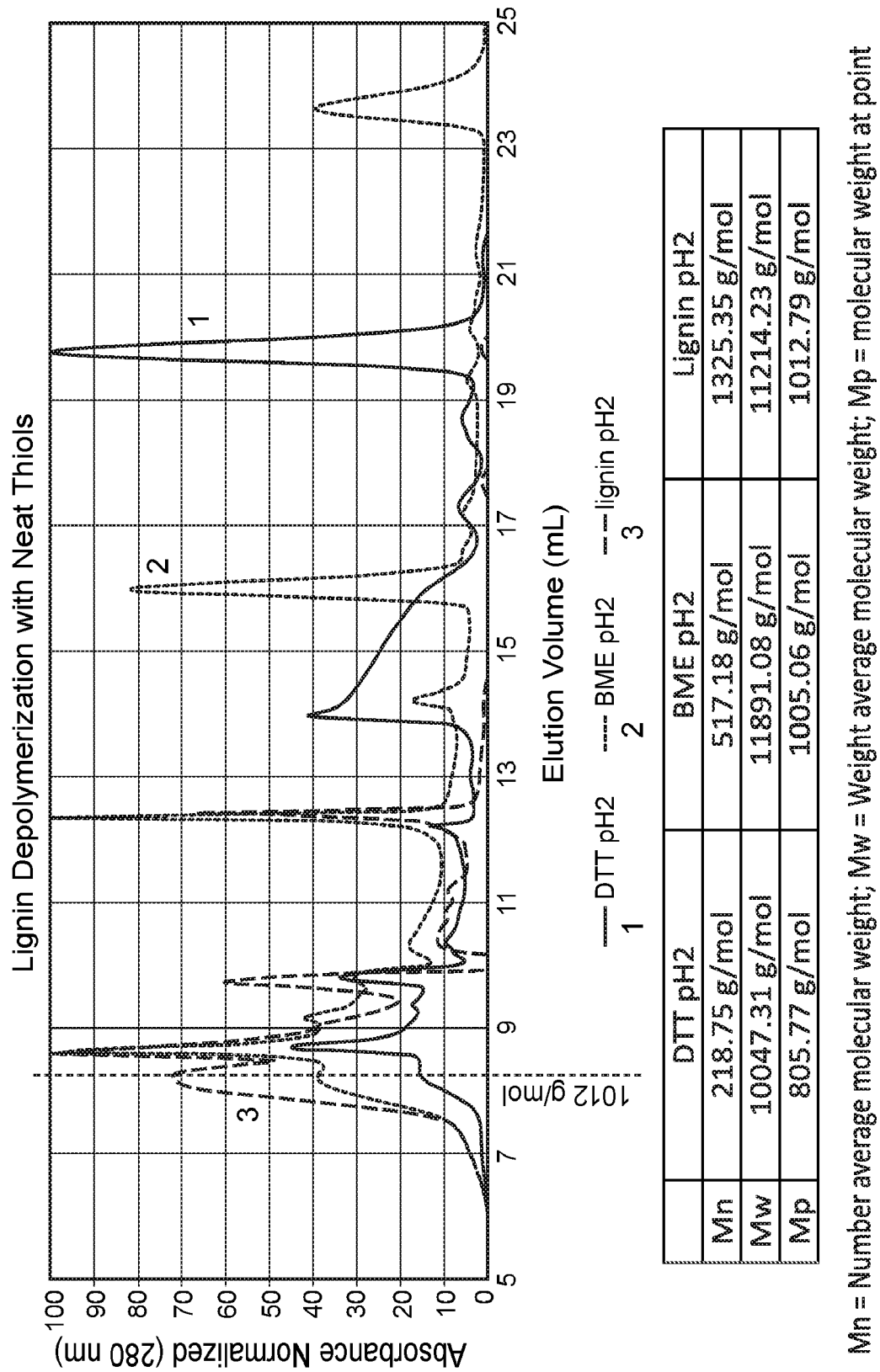
Figure 4D:
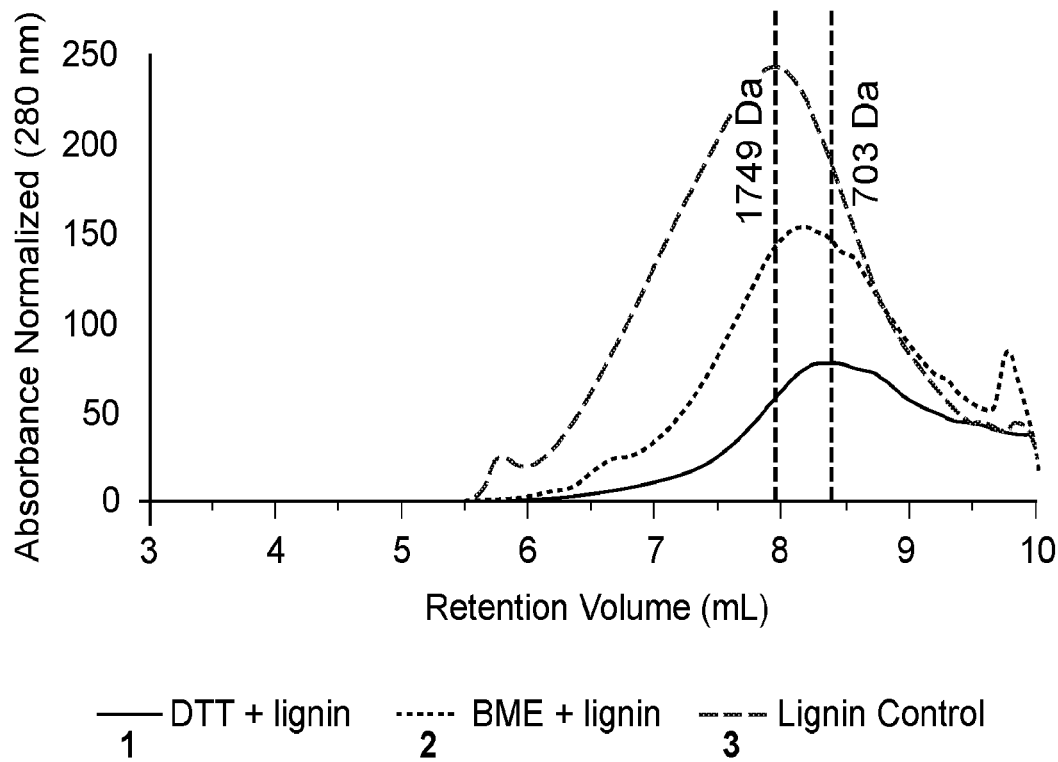

Additional reaction conditions (e.g. solvent, mole ratio of lignin model:thiol, reaction temperature, and reaction time) were explored for the four tested small thiol mediators (i.e., β-mercaptoethanol, dithiothreitol, 1,3-propanedithiol, and thiophenol) and glutathione, as shown in FIG. 3. For the data in FIG. 3, lignin model dimers (10 mg) and solid base (100 mg) were added to a round bottom (50 mL) equipped with a stir bar, condenser, septum, and nitrogen balloon, and purged with nitrogen. Solvent (20 mL) and thiol (1:1, 1:2, 1:10, and 1:100 dimer to thiol mole ratio) were added through a septum and the reaction was heated to the desired temperature with periodic sampling to monitor progress over 24-48 hrs with an HPLC. The table in FIG. 3 indicates the solvent: methanol (MeOH), dimethyl sulfoxide (DMSO), N-methyl-2-pyrrolidone (NMP), dimethylformamide (DMF), acetonitrile (MeCN), or no solvent (neat). FIG. 3 also indicates the thiol: dithiothreitol (DTT), β-mercaptoethanol (BME), thiophenol, glutathione, or 1,3-propanedithiol.

FIG. 3 also indicates the mole ratio of lignin model substrate to thiol. FIG. 3 also indicates the reaction temperatures at a specific value (° C.), at room temperature (RT), or under reflux conditions (reflux). FIG. 3 also indicates the reaction time. The final three columns of FIG. 3 indicate the conversion of the dimer substrate, as well as the yield of the two dimer component products ("1" and "2").

Thus, Example 2 demonstrates good to excellent yields for ether cleavage using β-mercaptoethanol, dithiothreitol, 1,3-propanedithiol, and thiophenol. Dithiothreitol was a better mediator than 1,3-propanedithiol in this model system, with dithiothreitol yielding complete cleavage under neat conditions, while 1,3-propanedithiol yielded incomplete cleavage under neat conditions, neither of which produced unreacted thioether intermediate. Without intending to be bound by theory, this may be due to the lower energy required to form a dithiol, thus releasing the second lignin monomer. Dithiothreitol and β-mercaptoethanol achieved the highest yields of the small thiol mediators tested with various solvents, temperatures, and mole ratio of substrate to thiol, as shown in Tables 1, 2, and FIG. 3.

Example 3: Cleavage of Cu-AHP Lignin

Following the success of model lignin dimers, the substrate scope of the reaction was broadened to include real lignin, obtained from the copper-catalyzed alkaline hydrogen peroxide (Cu-AHP) pretreatment of hybrid poplar. In this pretreatment, 100 g of poplar was incubated with aqueous 270 mM NaOH at 10% solids loading (1 liter) at 30° C. shaking for 1 hour. The biomass was washed with 500 mL deionized water and pretreated for an additional 23 hours at 10% solids loading (1 liter) with additional 270 mM NaOH, 1 mM copper, 2 mM bipyridine, and hydrogen peroxide (100 mg $H_2O_2$ per g of biomass added over the course of 10 hours). The mixture was then filtered to remove the solid biomass, and acid insoluble lignin was precipitated from the filtrate by lowering the pH to 2 with $H_2SO_4$. The precipitated lignin was centrifuged and washed 3 times with pH 2 water, frozen, and lyophilized to yield a light-yellow powder. The powder was then used for the subsequent depolymerization studies.

This lignin is a more oxidized version of the original lignin polymer. This is advantageous in the thiol biomimetic setup because it allows the direct cleavage of the β-O-4 linkage, skipping over the analogous dehydrogenase step that oxidizes the hydroxyl to a carbonyl, thus activating the β-carbon for attack.

Thiol-treated lignin was treated and processed as follows: 100 mg lignin and 100 mg potassium carbonate was added to a glass vial with a stir bar, capped with a septum, and purged with nitrogen. A 500 µL aliquot of either dithiothreitol (DTT) or β-mercaptoethanol (BME) was added and the reaction was stirred at 100° C. for 24 hours. After 24 hours, the reaction was quenched with 1) 20 mL water to a pH of 9, 2) with 20 mL water and 73% sulfuric acid to a pH of 7, or 3) 20 mL water and 73% sulfuric acid to a pH of 2. All reactions were run in duplicate. Molecular weight analysis was performed on a Waters GPC column, with conditions as stated under Reaction Protocol (above), for molecular weight comparisons. The aqueous solubilized thiol-treated lignin was also 1) precipitated with sulfuric acid to pH 2, frozen, and lyophilized for mass balance and thioacidolysis analysis; and 2) precipitated with hydrochloric acid to pH 2, frozen, and lyophilized for sulfur elemental analysis.

Under neat conditions, the lignin polymer had a molecular weight reduction of the most abundant peak of at least about 60% by GPC at pH 9, as shown in FIG. 4 (panel (A)), wherein the lignin had a starting number-average molecular weight of 7203.04 g/mol. Similar results were obtained when the thiol was quenched and adjusted to a pH of 7 or 2 with sulfuric acid, as seen in FIG. 4, panels (B) and (C), wherein the lignin had a starting Mn of 7127.76 g/mol and 1325.35 g/mol, respectively. FIG. 4, panel (D), presents further experiments at pH 9 in which the lignin polymer has a molecular weight reduction of the most abundant peak of about 60%, for example with a starting Mn of 8009 g/mol and a final Mn of 2583 g/mol (using DTT dithiol) or 3208 g/mol (using BME monothiol).

Figure 5:
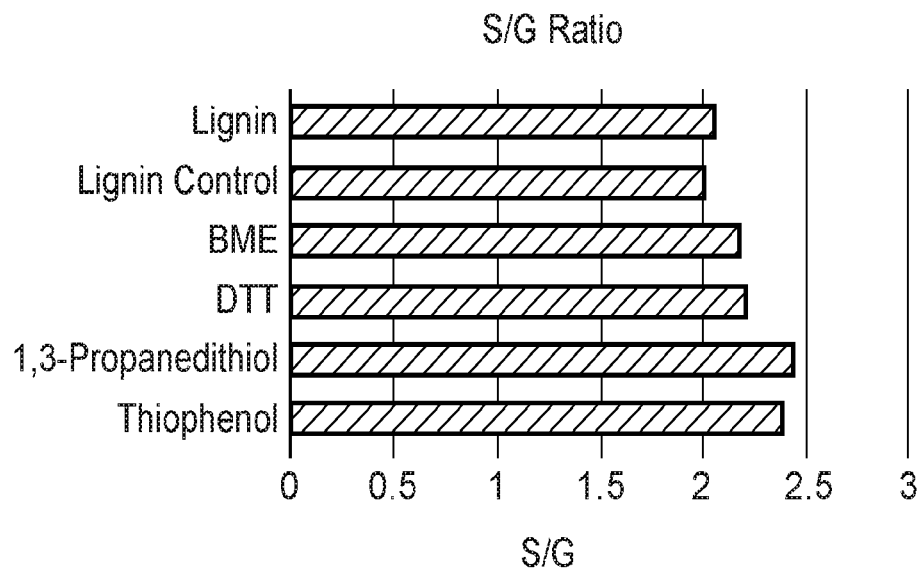
FIG. 5 shows the ratio of syringyl to guaiacyl (S:G) monomer units in a remaining lignin polymer after thiol treatment.
Figure 6:
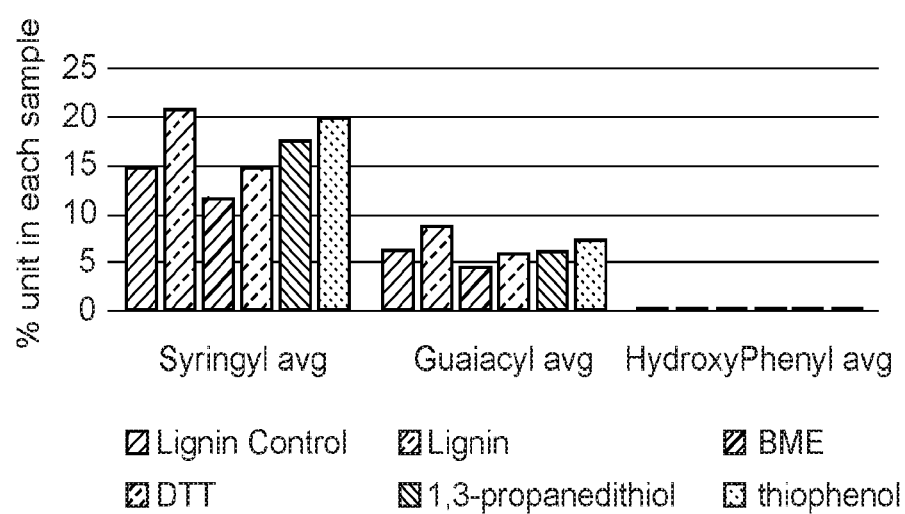
FIG. 6 shows the amount (%) of monomer units present in lignin polymer after thiol treatment.

Thioacidolysis of the remaining lignin polymer indicated no cleavage preference for syringyl (S) vs. guaiacyl (G) lignin fragments as shown by the S:G ratio of monomer units in the remaining lignin polymer after thiol treatment in FIG. 5. These results suggest little to no preference in lignin unit cleavage for S vs. G monomers. Furthermore, thioacidolysis of the remaining lignin polymer indicated that BME and DTT treated lignin have decreased S and G monomer yields (FIG. 6), suggesting that those monomers have already been cleaved during thiol treatment. Accordingly, without intending to be bound by theory, these results suggest that the thiol-treated lignin has fewer β-O-4 linkages remaining.

Example 4: Electrochemical Reduction of Thiol Compound

Upon cleavage of the lignin polymer, the oxidized thiol can be reduced using an electrochemical cell. The mechanism of this reaction, as shown in FIG. 7, involves two steps. The first is a one-electron addition to the disulfide, resulting in cleavage to form a thiolate and thiyl radical. The second step is another one-electron addition to the thiyl radical, forming a thiolate. The first step can occur via two mechanisms: stepwise or concerted. A stepwise mechanism involves radical anion formation, while a concerted mechanism allows for fragmentation, but requires more energy due to the bond dissociation energy. Initial studies of dithiothreitol in aqueous NaOH indicated an oxidized and reduced species when a voltage was applied to a single compartment electrochemical cell.

REFERENCES (1) U.S. Energy Information Administration. Monthly Energy Review, 2015. Web: http://www.eia.gov/totalenergy/data/monthly.
(2) Dale, B. E.; Holtzapple, M. The Need for Biofuels. *Chem Eng Prog.* 2015, 111, 36-40.
(3) Layton, B. E. A Comparison of Energy Densities of Prevalent Energy Sources in Units of Joules Per Cubic Meter. *Inter J Green Energy.* 2008, 5, 438-455.
(4) Botte, G. G. Electrochemical Manufacturing in the Chemical Industry. *The Electrochemical Society-Interface.* 2014, 49-55.
(5) Harmsen, P. F. H.; Huijgen, W. J. J.; Lopez, L. M. B.; Bakker, R. R. C. Literature Review of Physical and Chemical Pretreatment Processes for Lignocellulosic Biomass. *Biosynergy Project Review.* 2010, 1-49
(6) Wong, D. W. S. Structre and Action Mechanism of Ligninolytic Enzymes. *Appl Biochem Biotechnol.* 2009, 157, 174-209.
(7) Picart, P.; de Maria, P. D.; Schallmey, A. *Front Microbiol.* 2015, 6, 1-8.
(8) Zucca, P.; Rescigno, A.; Rinaldi, A. C.; Sanjust, E. Biomimetic metalloporphines and metalloporphyrins as potential tools for delignification: Molecular mechanisms and application perspectives. *J Mol Catal A-Chem.* 2014, 388-389, 2-34.
(9) Lange, H.; Decina, S.; Crestini, C. Oxidative upgrade of lignin-Recent routes reviewed. *Eur Polym J.* 2013, 49, 1151-1173.
(10) Li, C.; Zhao, X.; Wang, A.; Huber, G. W.; Zhang, T. Catalytic Transformation of Lignin for the Production of Chemicals and Fuels. *Chem Rev.* 2015, 115, 11559-11624.
(11) Mota, M. I. F.; Rodrigues Pinto, P. C.; Loureiro, J. M.; Rodrigues, A. E. Recovery of Vanillin and Syringaldehyde from Lignin Oxidation: A Review of Separation and Purification Processes. *Sep Purif Rev.* 2016, 45, 227-259.
(12) Rolando, C.; Monties, B.; Lapierre, C. Chapter 23: Thioacidolysis. *Wood Science: Methods in Lignin Chemistry.* Lin, S. Y.; Dence, C. W.; Springer: Verlag Berlin Heidelberg, 1992; pp 334-349.
(13) Crestini, C.; Caponi, M. C.; Argyropoulos, D. S.; Saladino, R. *Bioorg Med Chem.* 2006, 14, 5292-5302.
(14) Nagieb, Z. A. Demethylation of thiolignin by reaction with potassium dichromate—a kinetic study. *Wood Sci Technol.* 1985, 19, 233-242.
(15) Hu, L.; Pan, H.; Zhou, Y.; Hse, C.; Liu, C.; Zhang, B.; Xu, B. Chemical Groups and Structural Characterization of Lignin via Thiol-Mediated Demethylation. *J Wood Chem Technol.* 2014, 34, 122-134.
(16) Glass, R. S.; Hao, T. Chapter 27: Sulfur-, Selenium-, and Tellurium-Containing Compounds. *Organic Electro-* chemistry, 5th ed; Hammerich, O.; Speiser, B.; CRC Press—Taylor & Francis Group: Boca Raton, Fla., 2015; pp 1035-1102.
(17) Sequeira, C. A. C.; Santos, D. M. F. Electrochemical Routes for Industrial Synthesis. *J Braz Chem Soc.* 2009, 20, 387-406.
(18) Helmich, K. E.; Pereira, J. H.; Gall, D. L.; Heins, R. A.; McAndrew, R. P.; Bingman, C.; Deng, K.; Holland, K. C.; Noguera, D. R.; Simmons, B. A.; Sale, K. L.; Ralph, J.; Donohue, T. J.; Adams, P. D.; Phillips Jr., G. N. Structural Basis of Stereospecificity in the Bacterial Enzymatic Cleavage of 13-Aryl Ether Bonds in Lignin. *J. Biol Chem.* 2016, 291, 5234-5246.
(19) Trott, O.; Olson, A. J. AutoDock Vina: improving the speed and accuracy of docking with a new scoring function, efficient optimization and multithreading. *J Comput Chem.* 2010, 31, 455-461.
(20) Vedejs, E.; Eberlein, T. H.; Mazur, D J.; McClure, C. K.; Perry, D. A.; Ruggeri, R.; Schwartz, E.; Stults, J. S.; Varie, D. L.; Wilde, R. G.; Wittenberger, S. Thioaldehyde Diels-Alder Reactions, *J. Org. Chem.* 1986, 51, 1556-1562.

What is claimed is:

1. A method for depolymerizing lignin, the method comprising:
   reacting a lignin compound with a thiol compound to depolymerize the lignin compound and to form (i) a depolymerized lignin product having a reduced molecular weight relative to the lignin compound prior to reacting, and (ii) an oxidized thiol reaction product between two thiol groups from one or more thiol compounds; and
   reducing the oxidized thiol reaction product to form the thiol compound;
   wherein:
      the thiol compound comprises a hydrocarbon group having 1 to 8 carbon atoms and being substituted with 1 to 4 thiol groups.

2. The method of claim 1, wherein the lignin compound comprises a cross-linked phenolic polymer comprising at least one of β-O-4 ether linkages, α-O-4 ether linkages, 4-O-5 ether linkages, β-βcarbon-carbon linkages, β-1 carbon-carbon linkages, β-5 carbon-carbon linkages, and 5-5 carbon-carbon linkages between phenolic monomer units in the cross-linked phenolic polymer.

3. The method of claim 2, wherein the depolymerized lignin product has 50% or less linkages between phenolic monomer units in the cross-linked phenolic polymer relative to the lignin compound prior to reacting.

4. The method of claim 1, wherein the depolymerized lignin product has a molecular weight of 50% or less relative to the molecular weight of the lignin compound prior to reacting.

5. The method of claim 1, wherein the lignin compound prior to reacting has a number-average molecular weight of at least 400 g/mol.

6. The method of claim 1, wherein the lignin compound prior to reacting has a weight-average molecular weight of at least 10000 g/mol.

7. The method of claim 6, wherein the depolymerized lignin product has a weight-average molecular weight of 50% or less relative to the weight-average molecular weight of the lignin compound prior to reacting.

8. The method of claim 1, wherein the depolymerized lignin product comprises at least one of a lignin monomer unit and a lignin oligomer thereof, the lignin monomer unit comprising an aromatic group with one or more substituents selected from the group consisting of alcohol groups, ether groups, aldehyde groups, ketone groups, alkyl groups, carboxyl groups, and combinations thereof.

9. The method of claim 8, wherein the lignin monomer unit is selected from the group consisting of phenol, cresol, guaiacol, 4-ethyl-guaiacol, eugenol, isoeugenol, methoxyeugenol, syringol, and combinations thereof.

10. The method of claim 8, wherein the depolymerized lignin product is substantially free from adducts of the thiol compound with the lignin monomer unit or the lignin oligomer thereof.

11. The method of claim 1, wherein the thiol compound comprises a monothiol compound.

12. The method of claim 1, wherein the thiol compound comprises a hydrocarbon group having 1 to 6 carbon atoms and being substituted with 1 to 2 thiol groups.

13. The method of claim 1, comprising reacting the lignin compound with the thiol compound in a solvent reaction medium.

14. The method of claim 13, where the solvent reaction medium comprises a solvent selected from the group consisting of tetrahydrofuran (THF), dimethylformamide (DMF), acetonitrile (ACN), water, dioxane, and combinations thereof.

15. The method of claim 1, comprising reacting the lignin compound with the thiol compound at a temperature ranging from 20° C. to 200° C.

16. A method for depolymerizing lignin, the method comprising:
   reacting a lignin compound with a thiol compound to depolymerize the lignin compound and to form a depolymerized lignin product having a reduced molecular weight relative to the lignin compound prior to reacting;
   wherein:
      the lignin compound prior to reacting has a number-average molecular weight of at least 400 g/mol;
      the depolymerized lignin product has a number-average molecular weight of 50% or less relative to the number-average molecular weight of the lignin compound prior to reacting; and
      reacting the lignin compound with the thiol compound further comprises forming an oxidized thiol reaction product between two thiol groups from one or more thiol compounds.

17. A method for depolymerizing lignin, the method comprising:
   reacting a lignin compound with a thiol compound to depolymerize the lignin compound and to form (i) a depolymerized lignin product having a reduced molecular weight relative to the lignin compound prior to reacting, and (ii) an oxidized thiol reaction product between two thiol groups from one or more thiol compounds; and
   reducing the oxidized thiol reaction product to form the thiol compound;
   wherein:
      the thiol compound comprises a dithiol compound.

18. A method for depolymerizing lignin, the method comprising:
   reacting a lignin compound with a thiol compound to depolymerize the lignin compound and to form (i) a depolymerized lignin product having a reduced molecular weight relative to the lignin compound prior to reacting, and (ii) an oxidized thiol reaction product between two thiol groups from one or more thiol compounds; and reducing the oxidized thiol reaction product to re-form the thiol compound;

wherein:

the thiol compound comprises a hydrocarbon group having 1 to 8 carbon atoms and being substituted with 1 to 2 thiol groups;

the lignin compound comprises a cross-linked phenolic polymer comprising β-O-4 ether linkages, and the depolymerized lignin product has fewer β-O-4 ether linkages between phenolic monomer units in the cross-linked phenolic polymer relative to the lignin compound prior to reacting;

the depolymerized lignin product has a molecular weight of 50% or less relative to the molecular weight of the lignin compound prior to reacting; and the depolymerized lignin product comprises at least one of a lignin monomer unit and a lignin oligomer thereof, the lignin monomer unit comprising an aromatic group with one or more substituents selected from the group consisting of alcohol groups, ether groups, aldehyde groups, ketone groups, alkyl groups, carboxyl groups, and combinations thereof.

\* \* \* \* \*